(12) United States Patent
Allieri et al.

(10) Patent No.: US 11,053,214 B2
(45) Date of Patent: Jul. 6, 2021

(54) COMPOSITIONS AND METHODS RELATED TO PYRIDINOYLPIPERIDINE 5-HT$_{1F}$ AGONISTS

(71) Applicant: COLUCID PHARMACEUTICALS, INC., Indianapolis, IN (US)

(72) Inventors: Brigida Allieri, Verona (IT); Paul Fagan, Cambridge, MA (US); Emma Sharp, London (GB); Raymond D. Skwierczynski, Cambridge, MA (US)

(73) Assignee: CoLucid Pharmaceuticals, Inc., Indianapolis, IN (US)

( * ) Notice: Subject to any disclaimer, the term of this patent is extended or adjusted under 35 U.S.C. 154(b) by 0 days.

(21) Appl. No.: 16/467,208

(22) PCT Filed: Dec. 5, 2017

(86) PCT No.: PCT/US2017/064652
§ 371 (c)(1),
(2) Date: Jun. 6, 2019

(87) PCT Pub. No.: WO2018/106657
PCT Pub. Date: Jun. 14, 2018

(65) Prior Publication Data
US 2020/0087279 A1    Mar. 19, 2020

Related U.S. Application Data

(60) Provisional application No. 62/430,662, filed on Dec. 6, 2016.

(51) Int. Cl.
*C07D 401/06*    (2006.01)

(52) U.S. Cl.
CPC ........ *C07D 401/06* (2013.01); *C07B 2200/13* (2013.01)

(58) Field of Classification Search
CPC .................................................. C07D 401/06

USPC .......................................................... 546/194
See application file for complete search history.

(56) References Cited

U.S. PATENT DOCUMENTS

| 7,423,050 B2 | 9/2008 | Cohen et al. |
| 8,044,207 B2 | 10/2011 | Mancuso |
| 8,697,876 B2* | 4/2014 | Carniaux ............. C07D 401/06 546/194 |
| 8,748,459 B2 | 6/2014 | Cohen et al. |
| 2010/0256187 A1 | 10/2010 | Pilgrim et al. |
| 2013/0072524 A1 | 3/2013 | Carniaux et al. |
| 2014/0221385 A1 | 8/2014 | Hansen et al. |

FOREIGN PATENT DOCUMENTS

| EP | 1492786 B1 | 4/2006 |
| EP | 17829372.6 A1 | 7/2019 |
| EP | 17829372.6 A1 | 1/2020 |
| WO | WO 2003/084949 A1 | 10/2003 |
| WO | WO 2006/081127 A2 | 8/2006 |
| WO | WO 2010115125 A1 | 10/2010 |
| WO | WO 2011/123654 A1 | 10/2011 |
| WO | WO 2018010345 A1 | 1/2018 |
| WO | WO 2019/050759 A1 | 3/2019 |

OTHER PUBLICATIONS

International Search Report for PCT/US2017/064652, dated Feb. 21, 2018, Colucid Pharmaceuticals Inc.
IPRP, International Written Opinion for PCT/US2017/064652, dated Jun. 14, 2018, Colucid Pharmaceuticals Inc.
Caira, "Crystalline Polymorphism of Organic Compounds", Topics in Current Chemistry Springer Berlin, DE, vol. 198, Jan. 1, 1998, pp. 163-208.

* cited by examiner

*Primary Examiner* — Nizal S Chandrakumar
(74) *Attorney, Agent, or Firm* — Dan L Wood

(57) ABSTRACT

The present invention provides new pseudo-polymorphs of the hemisuccinate salt of 2,4,6-trifluoro-N-[6-(1-methyl-piperidine-4-carbonyl)-pyridin-2-yl]-benzamide which are useful in pharmaceutical compositions, for example, for the treatment and prevention of migraine headache.

7 Claims, 14 Drawing Sheets

Figure 1A. XRPD diffractogram of Form D of Compound I with peak 2θ identified
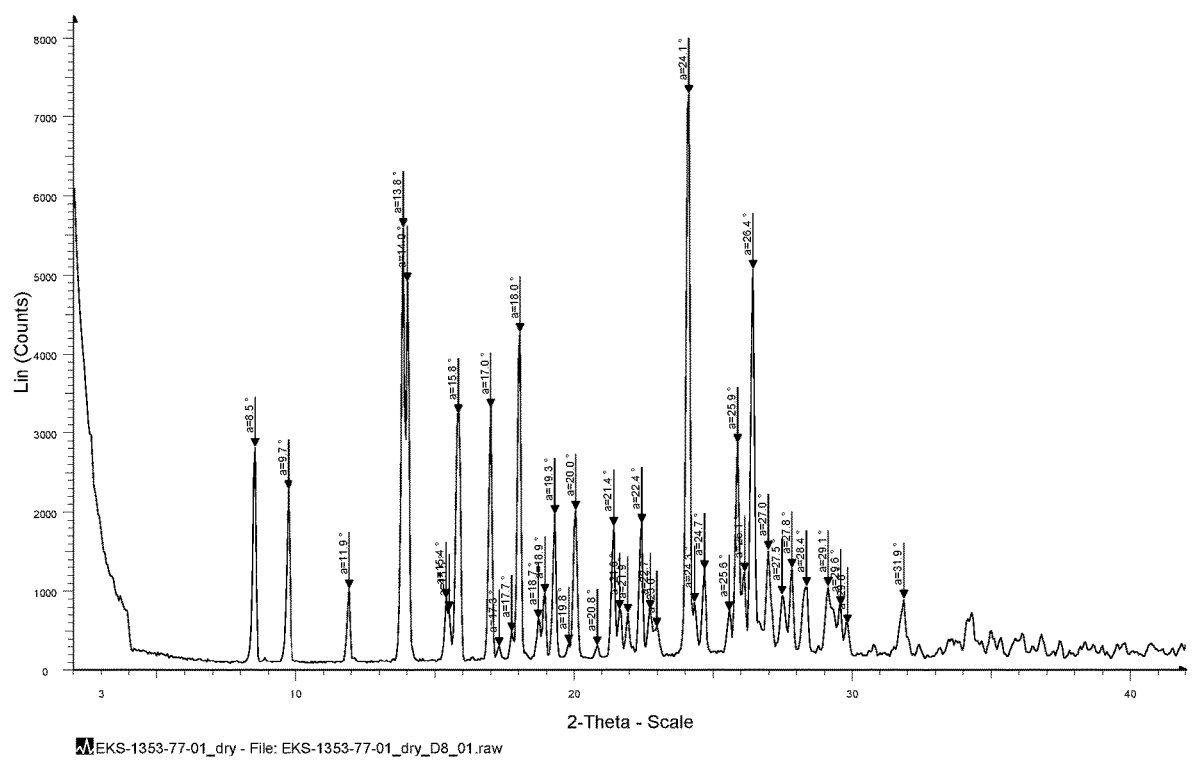

Figure 1B. XRPD diffractogram of Form F of Compound I
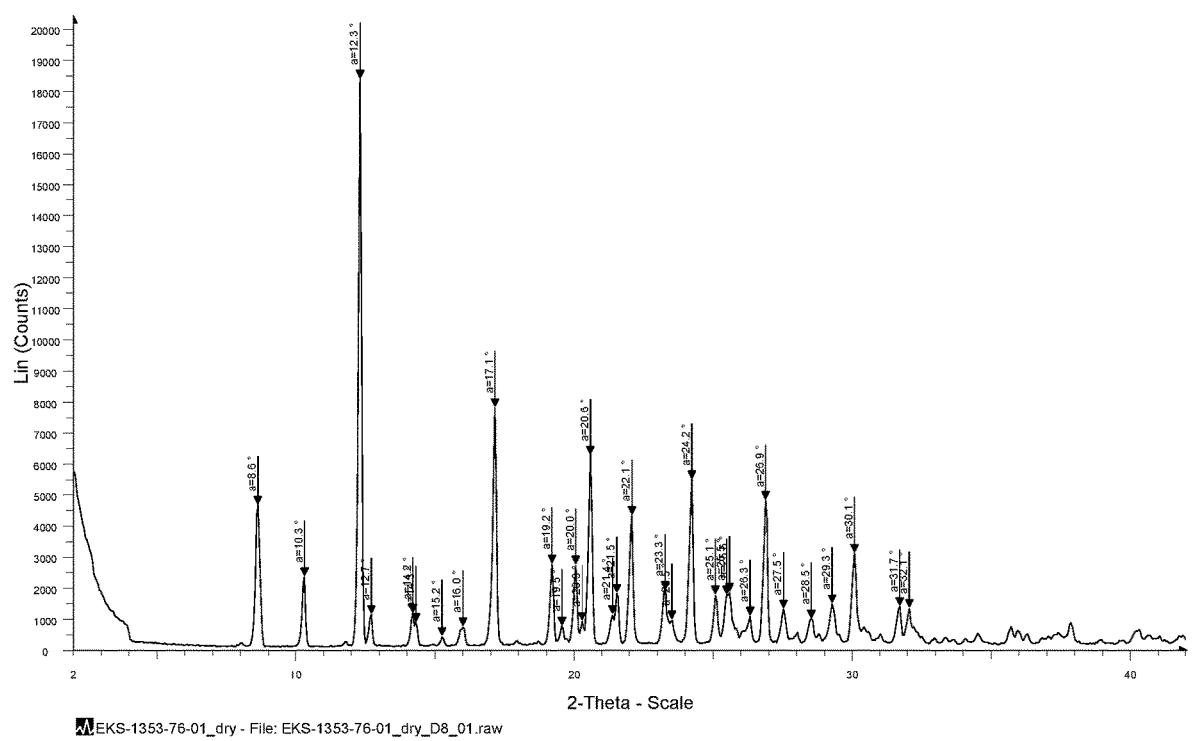

Figure 1C. XRPD of Form E of Compound I
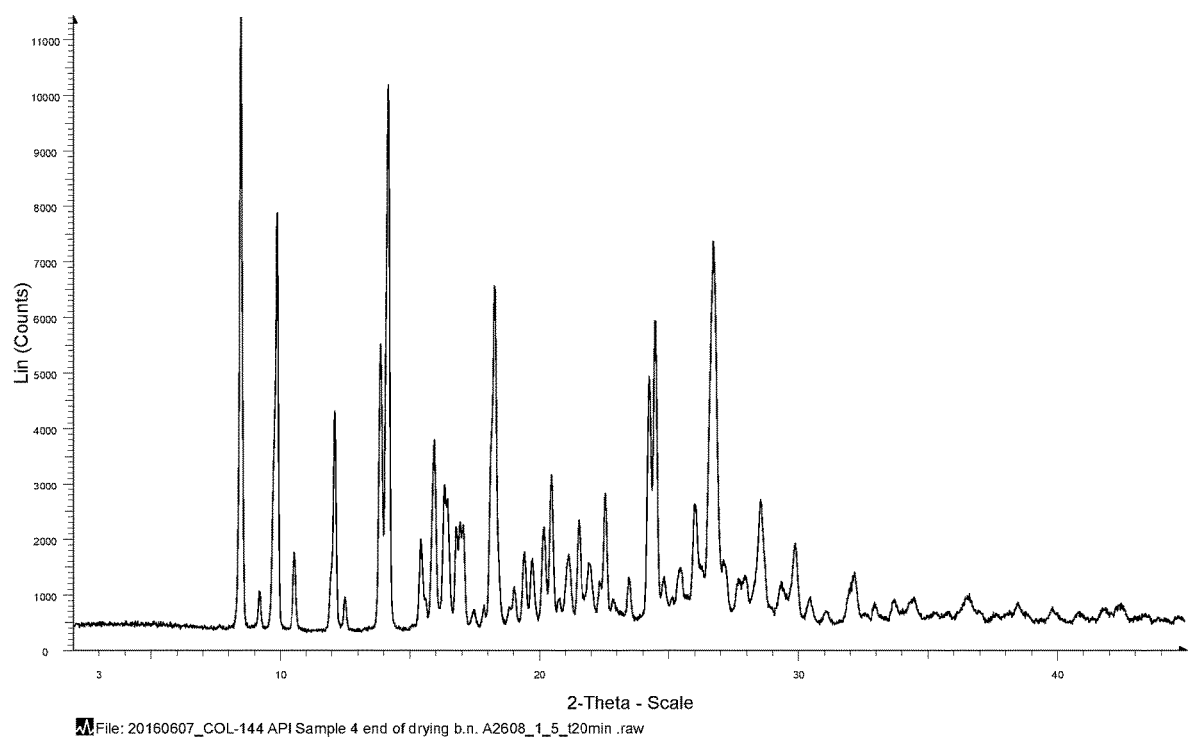

Figure 1D. SCXRD of Form D
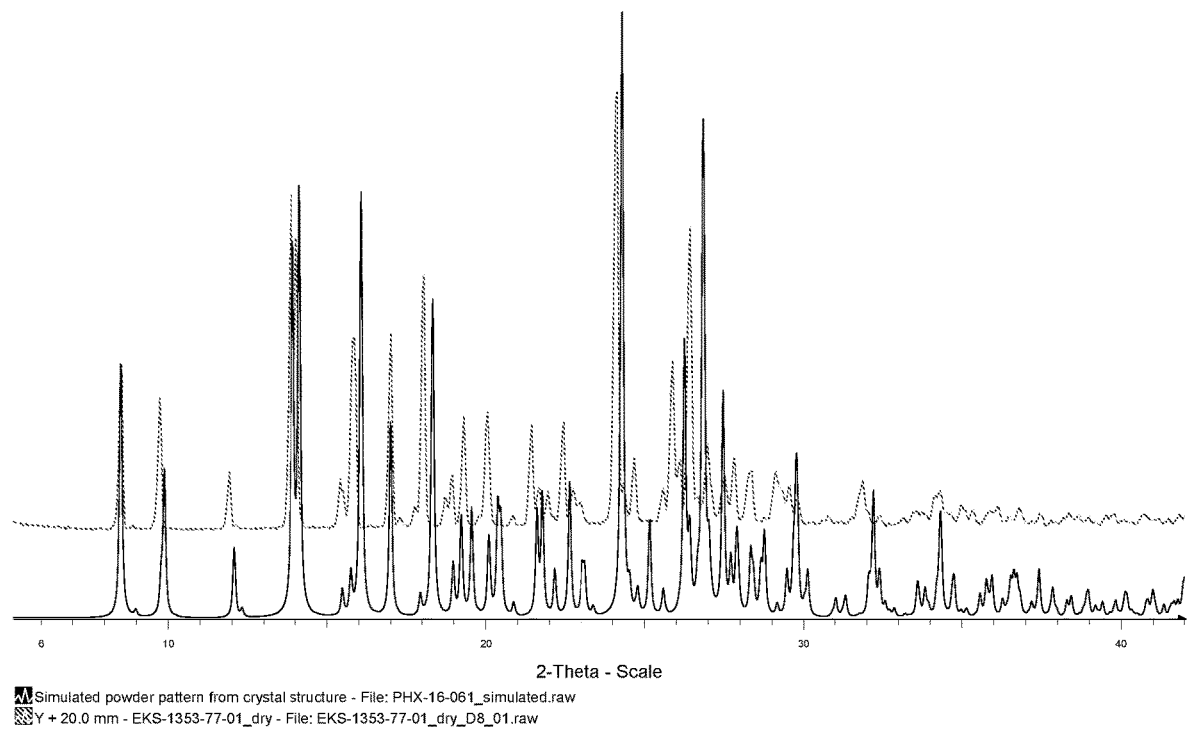

Figure 1E. Partial XRPD diffractogram (0 - ~13.5 °2θ)
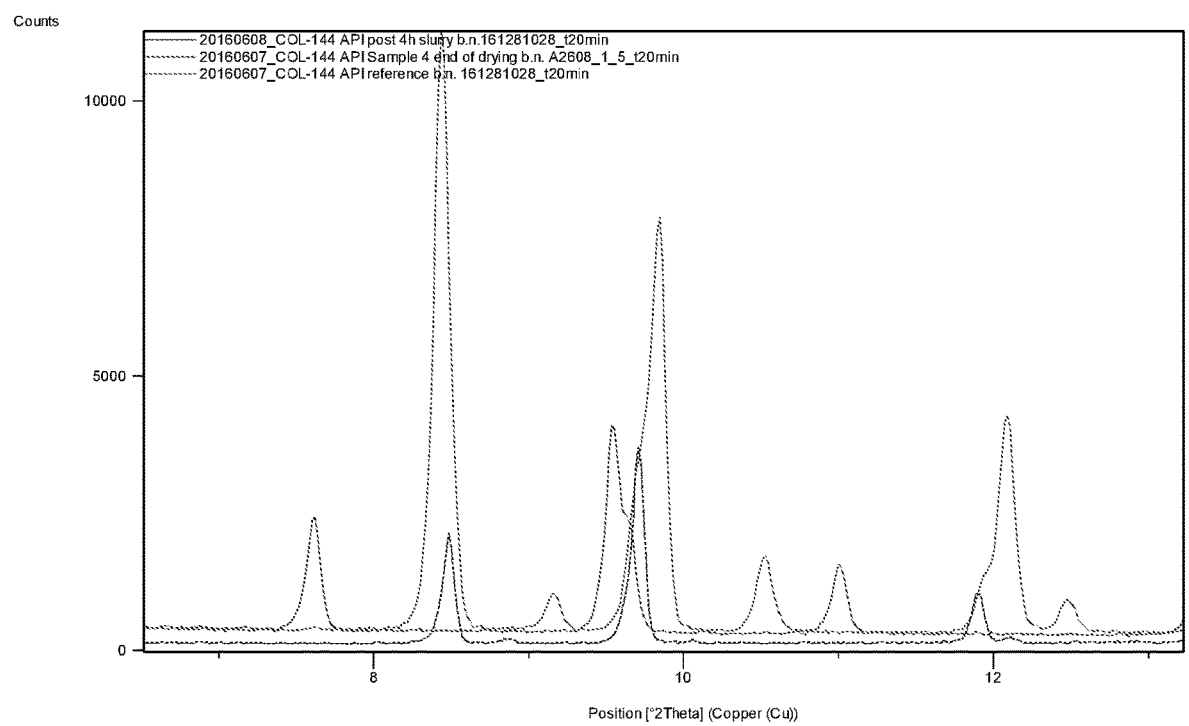

Figure 1F. Partial XRPD diffractogram (~12.5 °2θ - 19.5 °2θ)
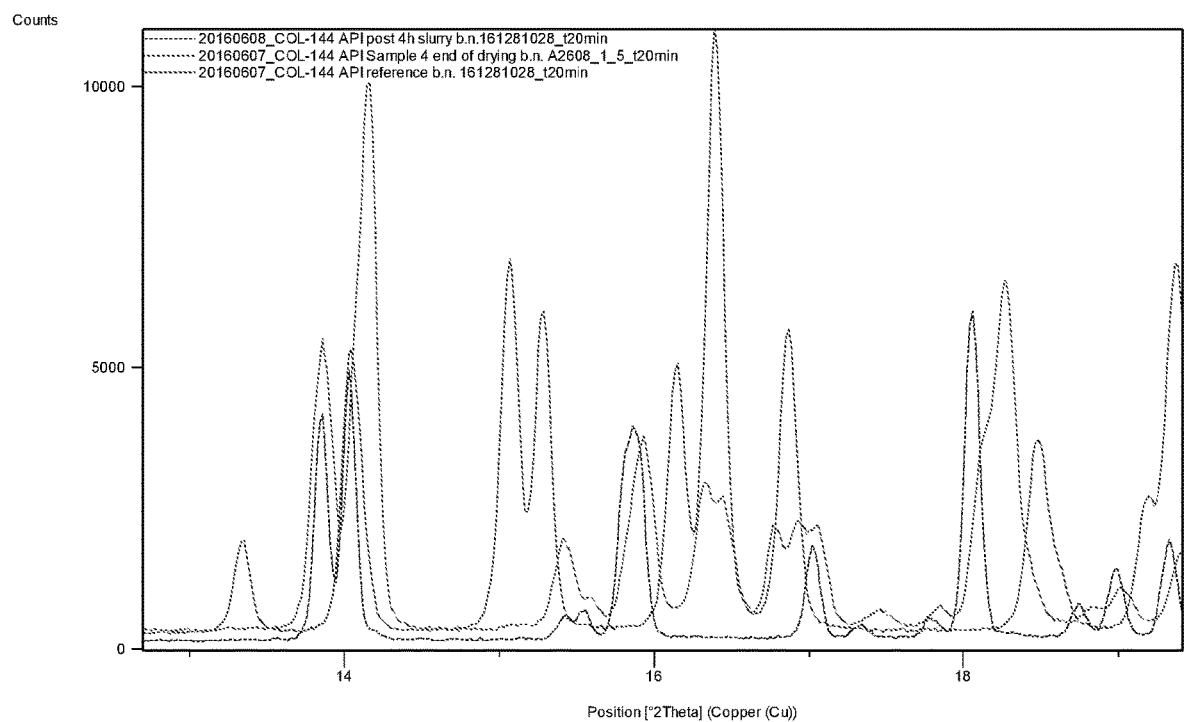

Figure 1G. Partial XRPD diffractogram (~18.5 °2θ - 25.5 °2θ)
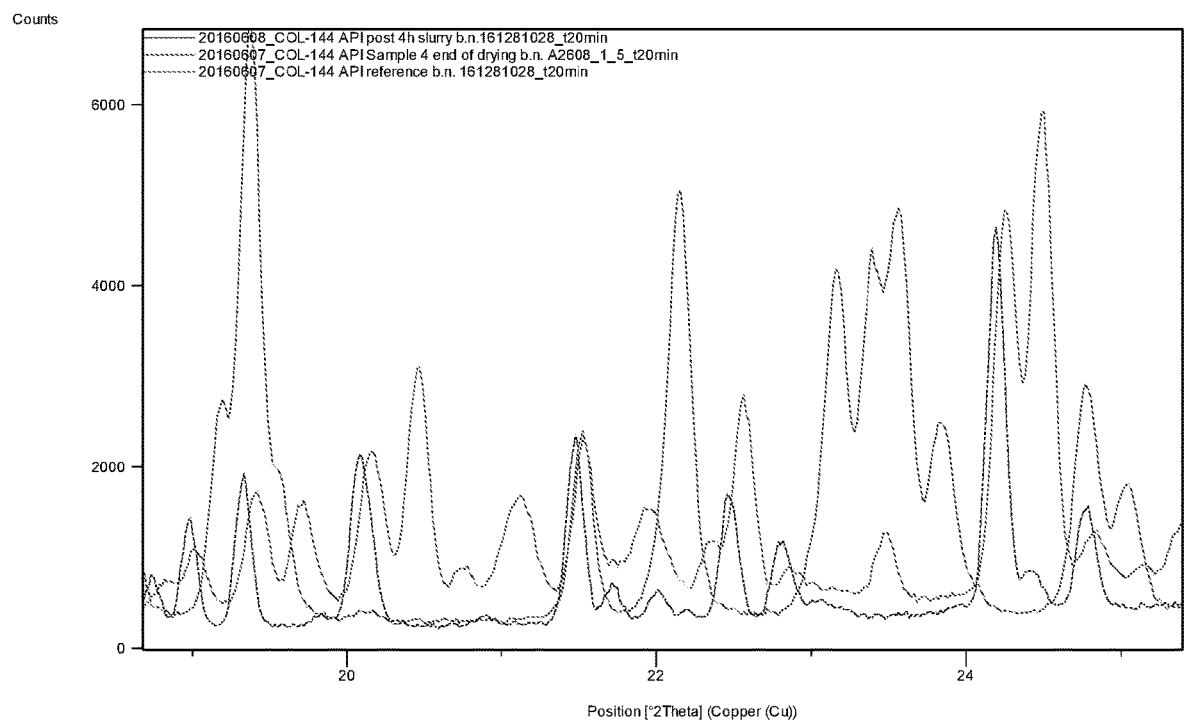

Figure 2. TGA and DSC of Form D
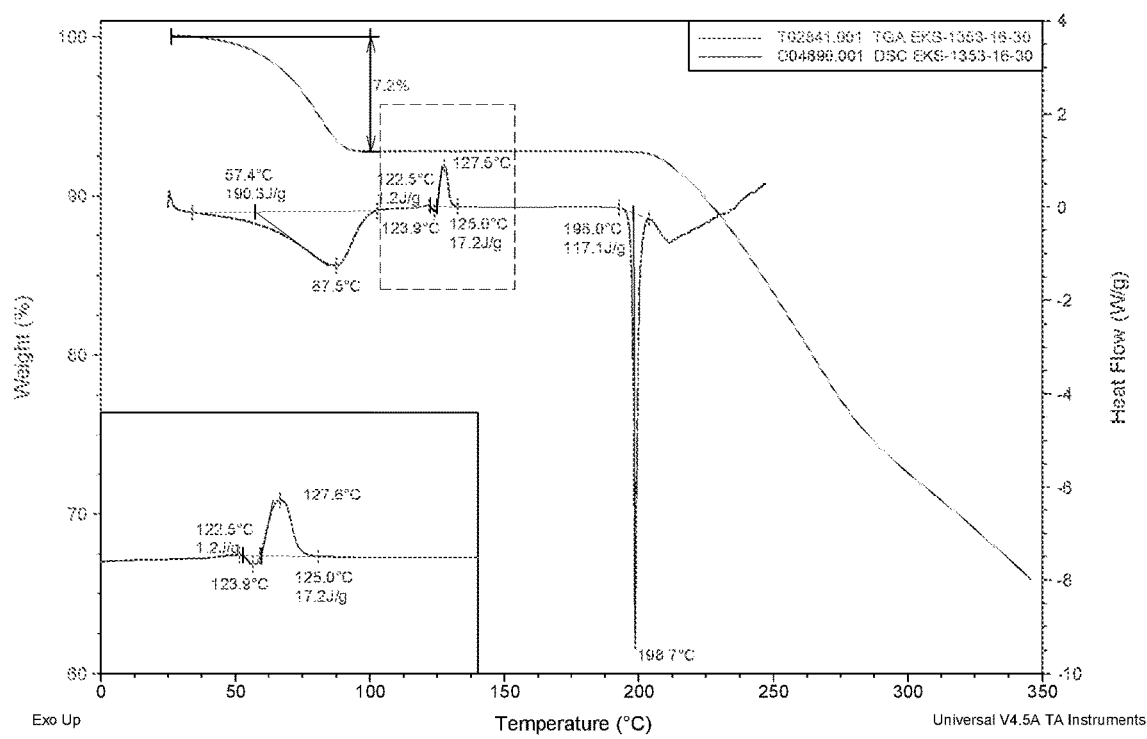

Figure 3. DSC thermogram and TGA analysis of Form F.
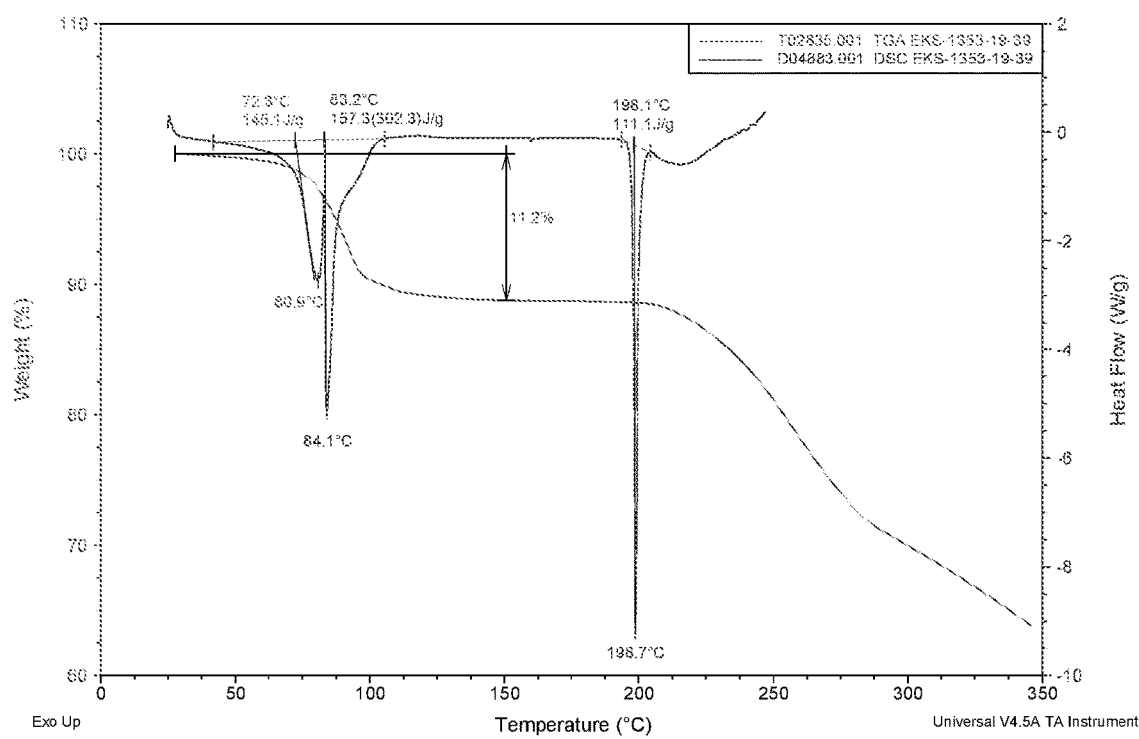

Figure 4A. Form D HPLC.
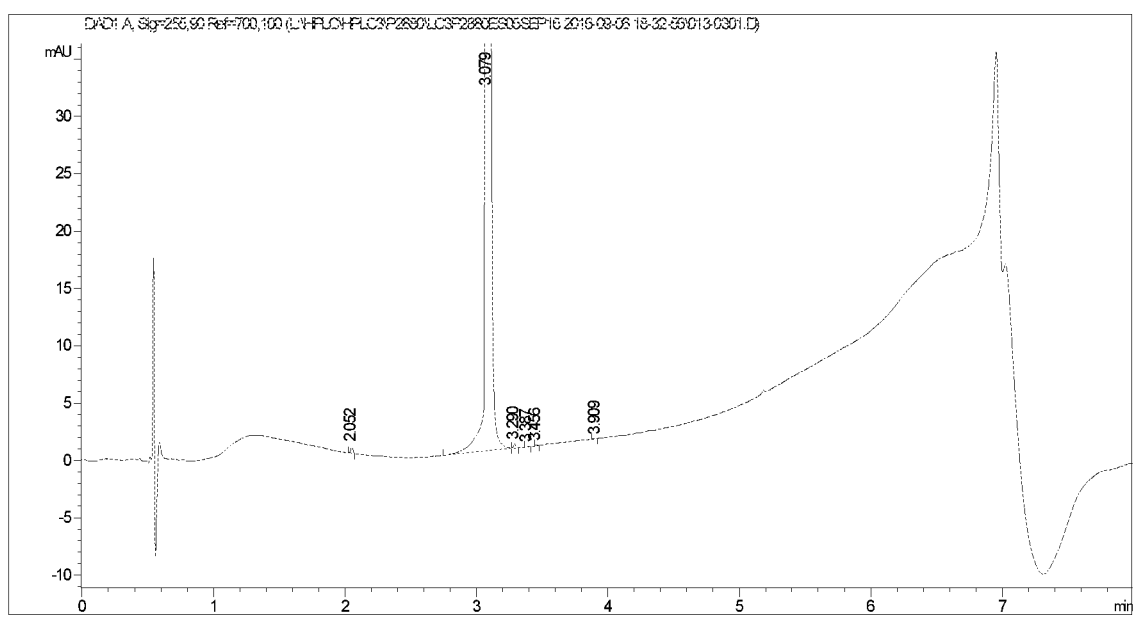

Figure 4B. Form F HPLC
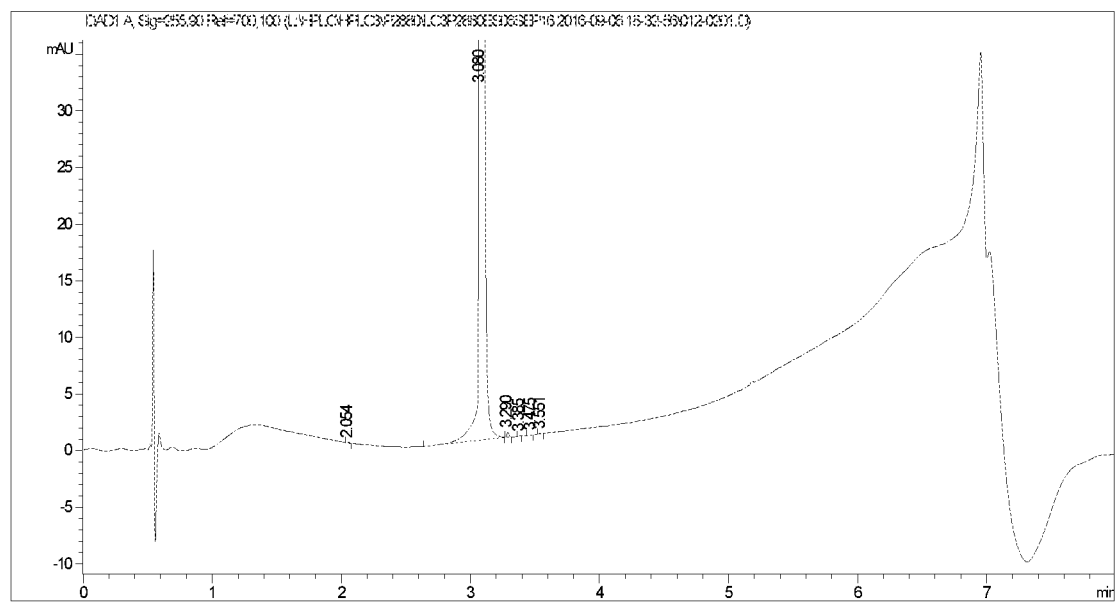

Figure 5. The solution state 1H-NMR spectrum of dissolved Form D or F of Compound I.
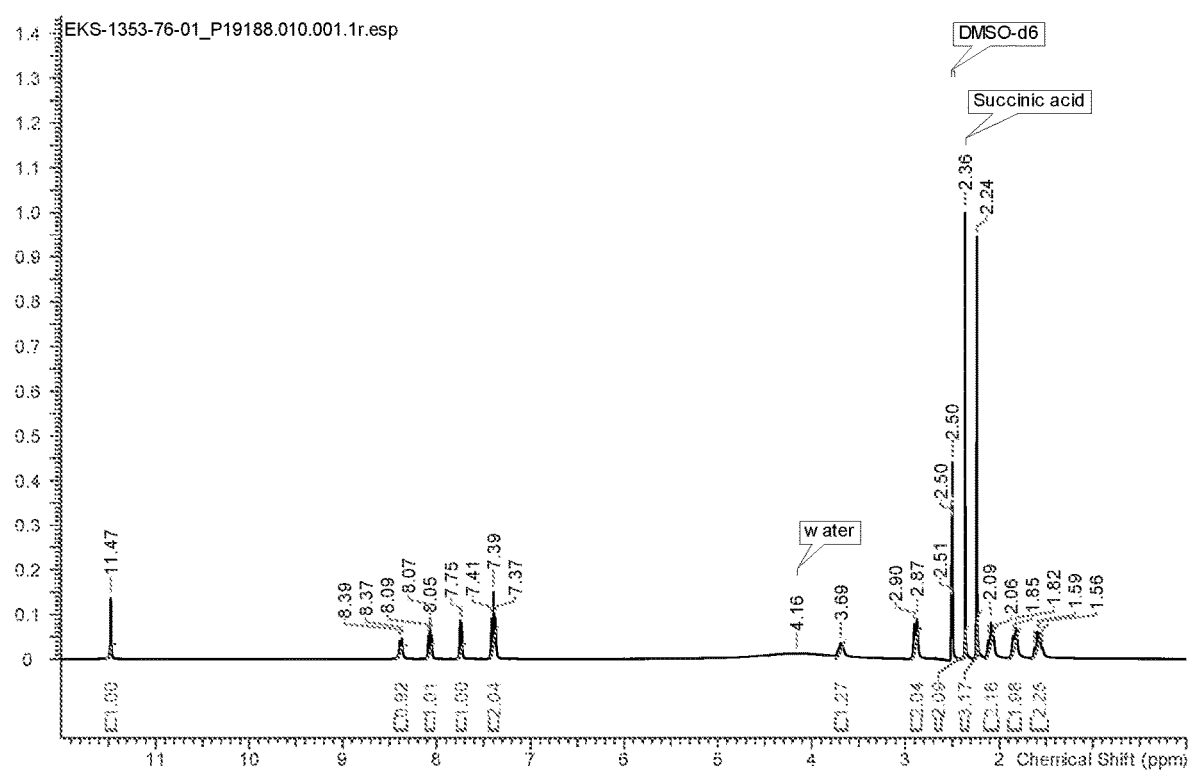

Figure 6. DVS Isotherm Plot for Form D
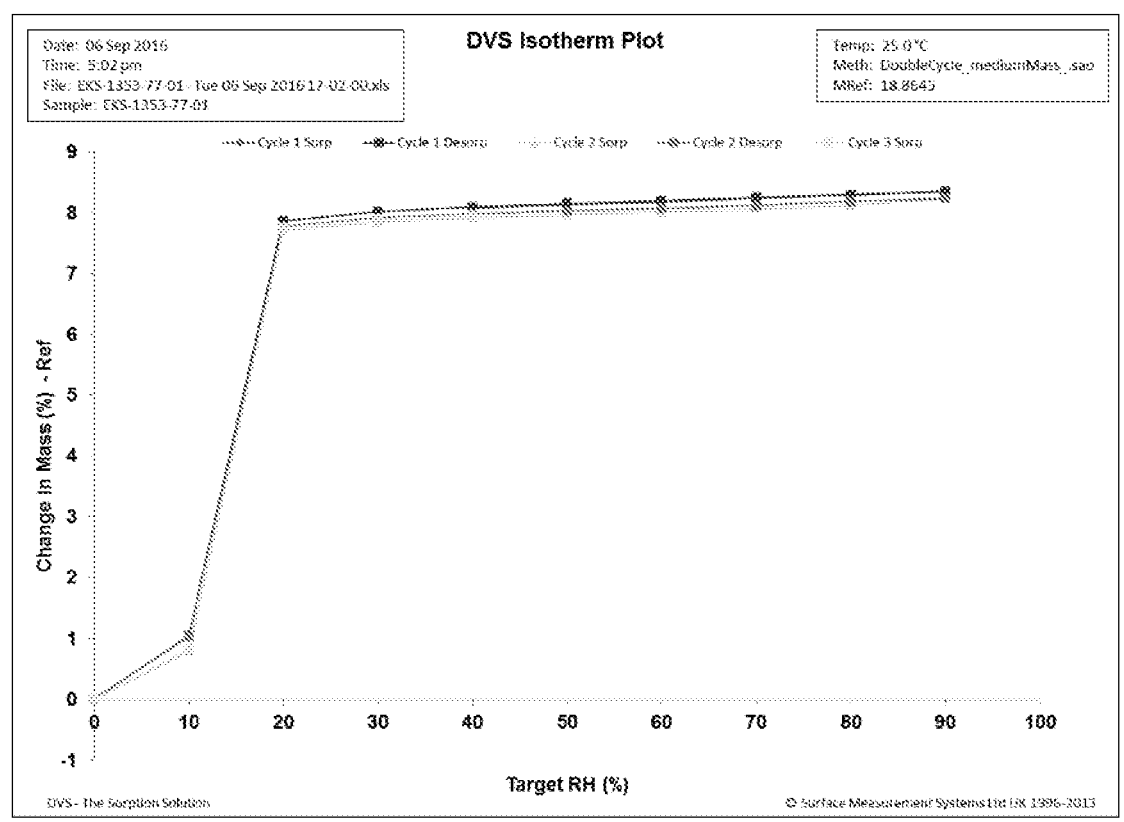

Figure 7. Form F
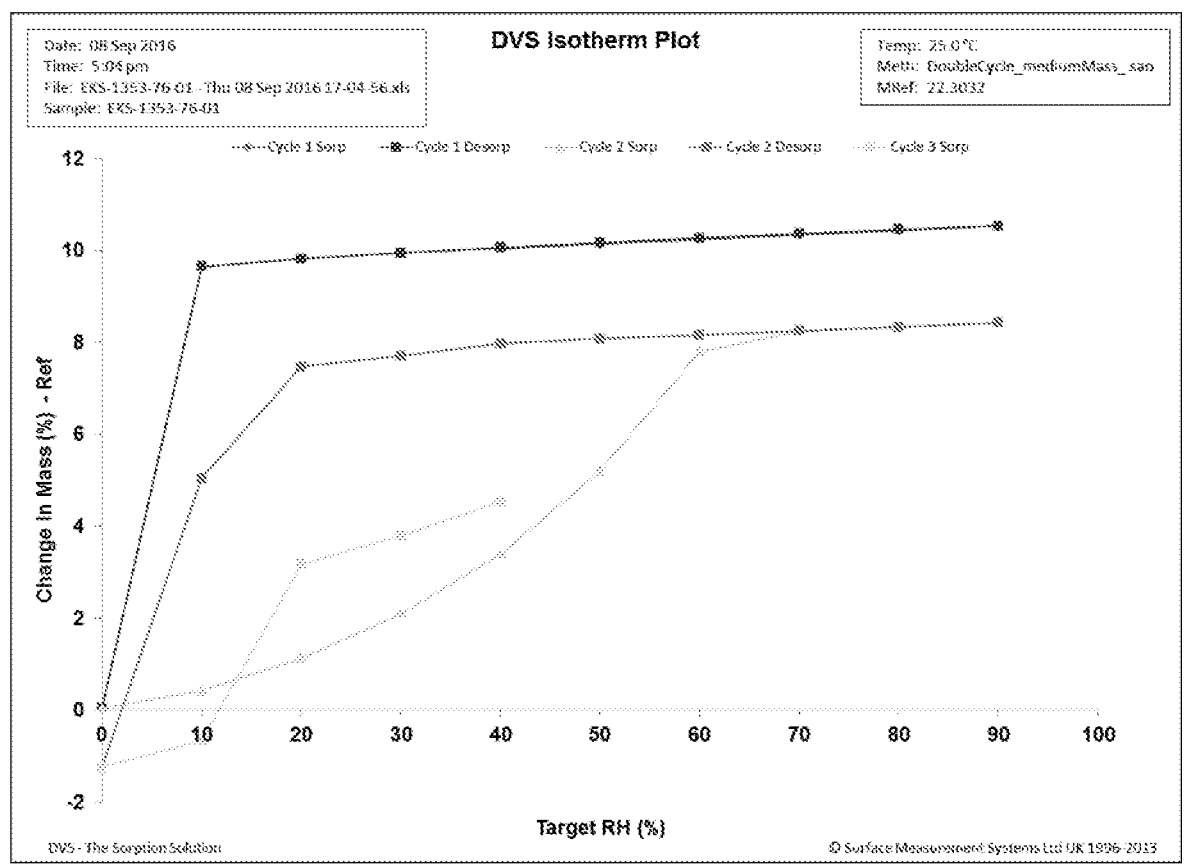

COMPOSITIONS AND METHODS RELATED TO PYRIDINOYLPIPERIDINE 5-$HT_{1F}$ AGONISTS

FIELD OF THE INVENTION

The present invention relates to certain solvates and other pseudo-polymorphic forms of the hemisuccinate salt of 2,4,6-trifluoro-N-[6-(1-methyl-piperidine-4-carbonyl)-pyridin-2-yl]-benzamide useful for activating 5-$HT_{1F}$ receptors and for the treatment or prevention of migraine.

BACKGROUND OF THE INVENTION

Migraine is a common and highly disabling brain disorder, affecting over 10% of adults globally (Stovner L I et al., Cephalalgia 2007; 27:193-210). The disease is typically characterized by attacks of 1-3 days of severe headache, associated with nausea, vomiting, photo- and phonophobia (migraine without aura), and, in one third of patients, neurological aura symptoms (migraine with aura) (Goadsby P J et al., N Engl J Med 2002; 346: 257-270). The pathogenesis of migraine is incompletely understood. Traditionally, vasodilation was considered pivotal in causing the headache in migraine (Wolff's Headache and Other Head Pain. Ed Silberstein et al., Oxford University Press, 2001). Triptans, selective 5-HT1B/1D receptor agonists with established antimigraine efficacy (Ferrari M D et al., Lancet 2001: 358; 1668-1675), were developed based on the assumption that 5-$HT_{1B}$ receptor-mediated cranial vasoconstriction is a prerequisite for antimigraine efficacy (Humphrey P P A et al., Ann NY Acad Sci 1990; 600: 587-598). As a consequence, triptans also carry the risk of causing coronary vasoconstriction (MaassenVanDenBrink A et al., Circulation 1998; 98: 25-30) and are contraindicated in patients with cardio- and cerebrovascular disease. In addition, many patients using triptans report chest symptoms, which may mimic angina pectoris, causing anxiety and diagnostic confusion (Welch K M A et al., Cephalalgia 2000; 20: 687-95; Visser W H, et al., Cephalalgia 1996; 16: 554-559). Thus, novel anti-migraine treatments that are devoid of vasoconstrictor activity are warranted.

In recent decades, it has become evident that cranial vasodilation, if it happens at all during a migraine attack (Schoonman G G et al., Brain 2008; 131: 192-200), may only be a secondary phenomenon due to activation of the trigeminovascular system (Goadsby P J et al., N Engl J Med 2002; 346: 257-270). Vasoconstriction may thus not be necessary to treat migraine headaches. Rather, neural inhibition of trigeminal pathways would provide an attractive alternative non-vascular antimigraine mechanism. Indeed, LY334370, a neurally active selective 5-$HT_{1F}$ receptor agonist with no vasoconstrictor activity at clinically relevant concentrations, proved effective in the acute treatment of migraine in an early clinical proof-of-concept study (Goldstein D J et al., Lancet 2001; 358: 1230-4). Unfortunately, the clinical development of LY334370 had to be stopped because of compound-specific safety concerns on long term exposure in animals.

2,4,6-trifluoro-N-[6-(1-methyl-piperidin-4-ylcarbonyl)-pyridin-2-yl]-benzamide (Compound I) is a new selective and highly potent 5-$HT_{1F}$ receptor agonist, with a Ki at human 5-$HT_{1F}$ receptors of 2.21 nM and an affinity which is more than 450-fold higher for 5-$HT_{1F}$ receptors than for other 5-$HT_1$ receptor subtypes (Nelson D L et al., Cephalalgia 2009: 29; 122). U.S. Pat. No. 7,423,050 and U.S. Publication No. 20080300407 describe Compound I, and other selective pyridinoylpiperidine 5-$HT_{1F}$ agonists, which are active in neurally mediated preclinical models of migraine, without causing vasoconstriction (i.e., neutrally active anti-migraine agents (NAANAs)). Experiments in the above-referenced publications demonstrate potent inhibition of c-Fos induction in the trigeminal nucleus caudalis and inhibition of dural plasma protein extravasation following electrical stimulation of the trigeminal ganglion. At concentrations up to 0.1 mM, Compound I did not constrict rabbit saphenous vein, a surrogate assay for human coronary vasoconstrictor liability (Nelson D L et al., Cephalalgia 2009: 29; 122).

Crystallinity of drugs affects, among other physical and mechanical properties, their solubility, dissolution rate, hardness, compressability and melting point. Because these properties may, in turn, affect a drug's manufacture and its utility, there is an existing need in the chemical and therapeutic arts for identification of crystalline forms of drugs and ways of making them. A crystalline form of the hemisuccinate salt of 2,4,6-trifluoro-N-[6-(1-methyl-piperidine-4-carbonyl)-pyridin-2-yl]-benzamide has been characterized and is referred to as Form A. See U.S. Pat. No. 8,697,876.

In addition to different solid crystalline forms, which are generally referred to as polymorphs, a drug may also exist in different pseudo-polymorphic forms, such as solvates and clathrates. The term solvate encompasses the compound formed by the association of one or more solvent molecules with the drug molecule. The term solvate includes hydrates, which refer to a stoichiometric or non-stoichiometric amount of water bound by non-covalent intermolecular forces, e.g., a hemi-hydrate, mono-hydrate, dihydrate, trihydrate, tetrahydrate, etc. The term clathrate refers to drug in the form of a crystal lattice that contains spaces (e.g., channels) that have a guest molecule (e.g., a solvent or water) trapped within.

Polymorphic and pseudo-polymorphic forms occur where the same composition of matter crystallizes in a different lattice arrangement resulting in different thermodynamic properties and stabilities specific to the particular polymorph form. In cases where two or more polymorph substances can be produced, it is desirable to have a method to make both polymorphs in pure form. In deciding which polymorph is preferable, the numerous properties of the polymorphs must be compared and the preferred polymorph chosen based on the many physical property variables. It is entirely possible that one polymorph form can be preferable in some circumstances where certain aspects such as ease of preparation, stability, etc. are deemed to be critical. In other situations, a different polymorph maybe preferred for greater or lesser solubility and/or superior pharmacokinetics. A particular crystalline form of a compound may have physical properties that differ from those of other polymorphic forms and such properties may influence markedly the physico-chemical and pharmaceutical processing of the compound, particularly when the compound is prepared or used on a commercial scale.

There are strict regulatory requirements for drugs intended for pharmaceutical use which mandate, among other things, a definitive knowledge of the polymorphic or pseudo-polymorphic form of the active pharmaceutical ingredient ("API") in the dosage form. The importance of recognizing and controlling for solid form changes during drug development is recognized in the art. See, for example, the recent review by Newman and Wenslow (AAPS Open (2016) 2:2). Accordingly, there is a need for the characterization and control of the polymorphic and/or pseudo-polymorphic form of the API in the dosage form both to meet regulatory requirements and to ensure the quality and consistency of the final dosage form.

This application describes the identification and characterization of newly discovered pseudo-polymorphic forms of the hemisuccinate salt of 2,4,6-trifluoro-N-[6-(1-methyl-piperidine-4-carbonyl)-pyridin-2-yl]-benzamide, and how to control their presence in solid dosage forms.

SUMMARY OF THE INVENTION

The present invention relates to pseudo-polymorphic forms of the hemi-succinate salt of 2,4,6-trifluoro-N-[6-(1-methyl-piperidine-4-carbonyl)-pyridin-2-yl]-benzamide, also referred to herein as Compound I, or lasmitidan hemisuccinate. The pseudo-polymorphic forms of Compound I described here unexpectedly occurred during the process of manufacturing for commercial scale pharmaceutical production. The pseudo-polymorphic forms described here are useful for activating 5-HT$_{1F}$ receptors and for the treatment or prevention of migraine headache.

In embodiments, the disclosure provides Compound I in the form of a solvate. In embodiments, the solvate is a hydrate. In embodiments, the hydrate is a di-hydrate or a tri-hydrate. In embodiments, the disclosure provides a hydrate or dehydrated hydrate characterized by an X-ray powder diffraction (XRPD) pattern substantially similar to one of those set forth in FIG. 1.

FIG. 1A shows an XRPD pattern of Form D, a di-hydrate, also referred to as Hydrate 1, using Cu-K$_\alpha$ radiation. In embodiments, the XRPD pattern for Form D includes at least peaks at about 18.7, 26.5, 27.0, 27.5 and 27.8 degrees 2θ, +/−0.2 degrees. In embodiments, the XRPD pattern of Form D includes one or more additional peaks as set forth in Table 2. In embodiments, the disclosure provides Form D characterized by having unit cell parameters at 100 Kelvin of about a=25.08 Å, b=10.08 Å, c=20.84 Å, α=90°, β=123.71, and γ angle=90°.

FIG. 1B shows an XRPD pattern of Form F, a tri-hydrate. In embodiments, the XRPD pattern of Form F includes the peaks as set forth in Table 4.

FIG. 1C shows an XRPD pattern of Form E, a dehydrated Form D. In embodiments, the XRPD pattern for Form E using Cu-K$_\alpha$ radiation includes at least peaks at about 9.2 and 10.5 degrees 2θ, +/−0.2 degrees. In embodiments, the XRPD pattern of Form E includes the peaks as set forth in Table 3.

In embodiments, the disclosure provides Compound I in the form of a di-hydrate, Form D, a tri-hydrate, Form F, or a dehydrated hydrate of Form D, referred to herein as Form E. In embodiments, the disclosure provides a composition comprising a mixture of Form A and Form D, or a mixture of Form A and Form E, or a mixture of Form D and Form E, or a mixture of Form A, Form D, and Form E.

In embodiments, the disclosure provides Compound I in the form of the di-hydrate Form D characterized by a Differential Scanning Calorimetry (DSC) thermogram having a broad endotherm onset at 53.1° C. (−158.2 J/g), a broad exotherm onset at 92.1° C. (24.9 J/g), and a sharp endotherm onset at 197.9° C. (−119.0 J/g). In embodiments, Form D exhibits a DSC thermogram substantially in accordance with FIG. 2.

In embodiments, the disclosure provides Compound I in the form of the tri-hydrate Form F characterized by a DSC thermogram having a broad endotherm onset at 71.2° C. (−198.4 J/g), a shallow endotherm (2 peaks) onset at 95.7° C. (−6.4 J/g), a shallow exotherm (2 peaks) at 103.4° C. (26.9 J/g), and a sharp endotherm onset at 197.8° C. (−114.4 J/g). In embodiments, the disclosure provides Compound I in the form of the tri-hydrate Form F characterized by a DSC thermogram substantially in accordance with that shown in FIG. 3.

In embodiments, a pseudo-polymorphic form of Compound I described here is identifiable on the basis of a characteristic thermogravimetry curve, also referred to as thermogravimetric analysis (TGA). TGA is based on a continuous recording of mass changes of a sample of material as a function of a combination of temperature and time.

In an embodiment, the disclosure provides Compound I in the form of the di-hydrate Form D characterized by TGA as showing 7.5 wt % loss from 25-110° C., reflecting 2.0 mole equivalent water, with degradation beginning about 200° C., substantially in accordance with FIG. 2.

In an embodiment, the disclosure provides Compound I in the form of the tri-hydrate Form F characterized by TGA as showing 11.4 wt % loss from 25-150° C., reflecting 3.1 mole equivalent water, with degradation beginning about 200° C., substantially in accordance with FIG. 3.

In embodiments, the disclosure provides Compound I in the form of the dihydrate Form D characterized by an XRPD pattern using Cu-K$_\alpha$ radiation including peaks at about 18.7, 26.5, 27.0, 27.5 and 27.8 degrees 2θ, +/−0.2 degrees and a DSC thermogram having a broad endotherm onset at 53.1° C. (−158.2 J/g), a broad exotherm onset at 92.1° C. (24.9 J/g), and a sharp endotherm onset at 197.9° C. (−119.0 J/g).

In embodiments, the disclosure provides Compound I in the form of the dihydrate Form D characterized by an X-ray diffraction pattern substantially similar to that set forth in FIG. 1A and a DSC thermogram substantially similar to that set forth in FIG. 2.

In embodiments, the disclosure provides the Compound I in the form of a dihydrate (Form D) produced by a method comprising any one of the following (1) a wet granulation process starting with Form A, (2) storage of Form A at 25° C. and 96% relative humidity (RH), (3) recrystallization from solvent/water mixtures with high water activity, (4) storage of amorphous Compound I at 40° C. and 75% RH, (5) slurry of amorphous Compound I in solvent/water mixtures with high water activity, (6) forming a slurry of amorphous Compound I in water at room temperature or above, (7) forming a slurry of Form F in water at 37° C., (8) forming a competitive slurry of Form F, e.g. ethanol-water (50/50 v/v) at 20° C. Form A is an anhydrous solid crystalline form of Compound I.

In embodiments, the disclosure provides the Compound I in the form of a trihydrate (Form F) produced by a method comprising starting with amorphous Compound I and forming a slurry in water at 5° C.; or forming a competitive slurry starting with Form A seeded with Form F in water at 20° C., or in ethanol/water (50:50) at 5° C.

In accordance with the embodiments described herein, 2,4,6-trifluoro-N-[6-(1-methyl-piperidine-4-carbonyl)-pyridin-2-yl]-benzamide, and its hemisuccinate salt, Compound I, can be prepared by methods described in the art. For example, as described in U.S. Pat. Nos. 8,697,876 and 7,423,050.

The present disclosure also provides pharmaceutical compositions comprising Compound I in the form of a hydrate, such as a dihydrate or a trihydrate, or in the form of a dehydrated hydrate, including mixtures thereof, and a pharmaceutically acceptable carrier. In embodiments, the pharmaceutical composition comprises one or more of Form D, Form E, and Form F of Compound I. In embodiments, the pharmaceutical composition comprises a mixture selected from the group consisting of a mixture of Forms A and D, a mixture of Forms A and E, a mixture of Forms D and E, and a mixture of Forms A, D, and E.

In embodiments, the pharmaceutical composition is substantially free from impurities. In embodiments, the pharmaceutical composition comprises Form D of Compound I having a chemical purity of about 98%, about 99%, or about 99.9% as determined by HPLC. In embodiments, the pharmaceutical composition comprises Form F of Compound I having a chemical purity of about 98%, about 99%, or about 99.9% as determined by HPLC.

The present disclosure also provides methods of treating migraine in a mammal comprising administering to a mammal in need of such treatment an effective amount of a pseudo-polymorph of Compound I, as described herein, or mixtures thereof. In embodiments, the pseudo-polymorph of Compound I is selected from Form D, Form E, and Form F of Compound I, and mixtures thereof, either alone or in combination with Form A, as described herein. In embodiments of any of the methods described here, the pseudo-polymorph of Compound I is selected from Form D, Form E, and Form F of Compound I, and mixtures thereof, including mixtures of one or more of Forms D, E, and F with Form A, as described herein.

BRIEF DESCRIPTION OF THE FIGURES

FIG. 1A-G: X-ray powder diffraction patterns (XRPD) for various pseudo-polymorphic forms of Compound I (the hemisuccinate salt of 2,4,6-trifluoro-N-[6-(1-methyl-piperidine-4-carbonyl)-pyridin-2-yl]-benzamide). A, Form D (a di-hydrate); B, Form F (a tri-hydrate); C, Form E (dehydrated Form D); D, Experimental and calculated single crystal XRPD patterns of Form D; E, Partial section of XRPD diffraction pattern (0-13 °2θ), Form D (blue line), Form A (green), Form E (red); F, Partial section of XRPD diffraction pattern (13-19.5 °2θ), Form D (blue line), Form A (green), Form E (red); G, Partial section of XRPD diffraction pattern (18.5-26 °2θ), Form D (blue line), Form A (green), Form E (red).

FIG. 2: DSC thermogram and TGA analysis of Form D. Overlays of DSC (blue line, heat flow (W/g), lower trace and inset) and TGA (green, weight (%) scale, upper trace) results for Form D.

FIG. 3: DSC thermogram and TGA analysis of Form F. Overlays of DSC (blue line, heat flow (W/g), upper trace) and TGA (green, weight (%) scale, lower trace) results for Form F.

FIG. 4A-B: A, HPLC trace of Form D having showing a chemical purity of 99.93%; B, HPLC trace of Form F showing a chemical purity of 99.95%.

FIG. 5: The solution state $^1$H-NMR spectrum of dissolved Form D or F of Compound I.

FIG. 6: DVS Isotherm plot for Form D, showing 3 cycles of sorption/desorption, all of which are superimposable.

FIG. 7: DVS Isotherm plot for Form F, showing 3 cycles of sorption/desorption, Cycle 1 sorption and desorption lines are uppermost (red and blue) and essentially superimposable; Cycle 2 desorption line is second uppermost line (pink) sorption line (green) plotted from 0-~70% RH; cycle 3 sorption (turquoise) plotted from 0 to ~40% RH.

DETAILED DESCRIPTION OF THE INVENTION

Pyridinoylpiperidine compounds useful for activating the serotonin-1F (5-HT$_{1F}$) receptor and for the treatment or prevention of migraine, have been described, for example in U.S. Pat. No. 7,423,050 and US 2010/0256187. Such compounds include the hemisuccinate salt of 2,4,6-trifluoro-N-[6-(1-methyl-piperidine-4-carbonyl)-pyridin-2-yl]-benzamide ("Compound I"), which has the structural formula shown below and may also be referred to as lasmitidan hemisuccinate.

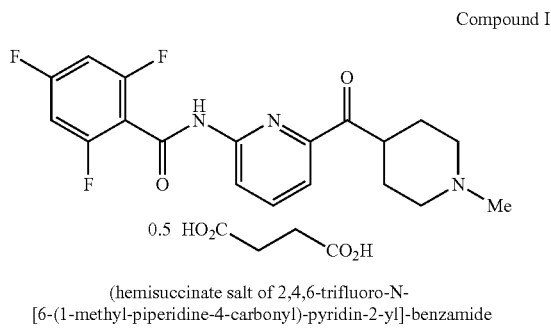

Compound I (hemisuccinate salt of 2,4,6-trifluoro-N-[6-(1-methyl-piperidine-4-carbonyl)-pyridin-2-yl]-benzamide Certain polymorphic forms of Compound I were also described in U.S. Pat. No. 8,697,876. One of the forms described is a polymorph referred to as Form A. Form A is an anhydrous solid crystalline form of Compound I. In accordance with the embodiments described herein, 2,4,6-trifluoro-N-[6-(1-methyl-piperidine-4-carbonyl)-pyridin-2-yl]-benzamide, its hemi-succinate salt (Compound I), and the anhydrous solid crystalline form of Compound I, referred to as Form A, can be prepared by methods described in the art, for example, as described in the '876 patent. The '876 patent describes two additional XRPD patterns designated Form B and Form C. No further characterization of those forms is available. For ease of reference, the present disclosure continues the naming pattern established in the '876 patent. Accordingly, new pseudo-polymorphic forms of Compound I described here are referred to as Form D, Form E, and Form F. Form D is also referred to as Hydrate 1 or the di-hydrate. Form E is also referred to as the dehydrated hydrate of Form D, and it may exist as a partially or fully dehydrated hydrate of Form D. Form F is also referred to as the tri-hydrate. The structure of Form F was determined based on weight-loss from a crystallization study.

Prior to the present disclosure, it was not known that Compound I can exist in the different pseudo-polymorphic forms described here. These pseudo-polymorphic forms were inadvertently discovered to occur during the process of manufacturing the product for commercial scale pharmaceutical production. Given that the regulatory agencies which oversee the approval and use of such pharmaceuticals require a definitive knowledge, characterization and control of the polymorphic form of the active component in solid pharmaceutical dosage forms, there is a need in the art for crystallization and characterization of these new polymorphic forms Compound I.

The terms "polymorphic form, polymorph, polymorph form, pseudo-polymorph, crystalline form, physical form or crystalline polymorph" of 2,4,6-trifluoro-N-[6-(1-methyl-piperidine-4-carbonyl)-pyridin-2-yl]-benzamide in the present invention refer to a crystal modification of this compound, which can be characterized by analytical methods such as X-ray powder diffraction pattern, (XRPD), differential scanning calorimetry (DSC), by thermogravimetric analysis (TGA) and gravimetric or dynamic vapor sorption (GVS; DVS).

The term "hydrate" as used herein means a compound of the invention or a salt thereof that further includes a stoichiometric or non-stoichiometric amount of water bound by non-covalent intermolecular forces. Hydrates are formed by the combination of one or more molecules of water with one molecule of the substances in which the water retains its molecular state as H$_2$O, such combination being able to form one or more hydrate. As used herein, a hydrate of Compound I is considered a "pseudo-polymorph", including the dehydrated hydrate described herein.

The pseudo-polymorphs described here may be characterized by any methodology according to the art. For example, the pseudo-polymorphs may be characterized by X-ray powder diffraction (XRPD), differential scanning calorimetry (DSC), thermogravimetric analysis (TGA), microscopy, and spectroscopy (e.g., nuclear magnetic resonance (NMR).

In embodiments, the pseudo-polymorphs are characterized by XRPD. The relative intensities of XRPD peaks can vary, depending upon the sample preparation technique, the sample mounting procedure and the particular instrument employed. Moreover, instrument variation and other factors can affect the 2-theta values. Therefore, the XRPD peak assignments can vary by plus or minus about 0.1, 0.2, 0.3, or 0.4 degrees. For instance, in some embodiments the 2-θ values of a Form described here may vary by plus or minus about 0.4 degrees. In other embodiments, the 2-θ values of a Form described here may vary by plus or minus about 0.2 degrees. In still other embodiments, the 2-θ values of a Form described here may vary by plus or minus about 0.1 degrees. Pharmaceutical compositions comprising a pseudo-polymorph described here can be identified by comparison of the compositions' X-ray powder diffraction patterns to an X-ray powder diffraction pattern of pure polymorph. It will be appreciated that pharmaceutical compositions comprising a particular pseudo-polymorph described here may exhibit non-identical X-ray powder diffraction patterns as compared to an X-ray powder diffraction pattern of the pure polymorph.

The pseudo-polymorphs described here can also be identified by characteristic differential calorimeter scanning (DSC) traces such as shown in the Figures. For DSC, it is known that the temperatures observed will depend upon the rate of temperature change as well as sample preparation technique and the particular instrument employed. Thus, the values reported herein relating to DSC thermograms can vary by plus or minus about 4, 6, 8 or 10° C. For instance, the values can vary by plus or minus about 6° C.

The pseudo-polymorphic forms of the invention may also give rise to thermal behavior different from that of the amorphous material or another polymorphic form. Thermal behavior may be measured in the laboratory by thermogravimetric analysis (TGA) which may be used to distinguish some polymorphic forms from others. In one aspect, the pseudo-polymorph may be characterized by thermogravimetric analysis.

Pseudo-polymorphs according to the invention can also be identified by gravimetric vapor sorption (GVS), which measures rate and amount of solvent absorption by a sample. In one aspect, the pseudo-polymorph may be characterized by gravimetric vapor sorption analysis.

Polymorph Formation

Crystallization solvent is an important factor in determining which polymorph or pseudo-polymorph of Compound I is formed. For example, solvents with low water activity, e.g. ethanol, give primarily Form A. Water content is also important because the different polymorphic forms have varying levels of hydration. In the mixtures of water and water miscible solvents, the amount of water can vary from about 6.1% by volume to about 95% by volume, preferably from about 10% to about 20% by volume, more preferably from about 5% to about 10% by volume and most preferably from about 5% to about 1% of water. Forms D and F of Compound I are hydrates, and thus there is a minimum threshold of water that must be present in order for Compound I to crystallize as either of these forms. In addition, the cooling rate and isolation temperature and amount of water may play a role in determining which polymorphic form and/or hydrate is formed, as described in more detail below.

It has been discovered that, starting with either Form A or the amorphous form of Compound I, addition of water alone or water/solvent mixtures results in the conversion from Form A or the amorphous form to one of the novel pseudo-polymorphic Forms D, E, or F. Form A is the dominant form in the absence of water (up to 10% by volume of water; a water activity of approximately 0.6) or at low water activities, e.g. in pure ethanol, at any temperature. At higher water activities, temperature and water content are determinative.

Conversion of Form A to Form D occurs as water is introduced, for example, through high humidity conditions or in solvent-water mixtures with a high water activity. Form D is the most stable form at intermediate water activities and higher temperatures (i.e. room temperature to approximately 40° C.).

In embodiments, the disclosure provides Compound I in the form of the di-hydrate Form D. Surface x-ray diffraction (SXRD) analysis of a single crystal of Compound I shows that it contains one molecule of Compound I, two molecules of water, and a half-molecule of succinate. A simulated powder pattern based on this crystal structure matches the XRPD for Form D, or Hydrate 1, presented in FIG. 1D, thus confirming that Form D is a di-hydrate of Compound I. The experimental pattern (RT) from the bulk sample is shown in red (top trace) and the pattern calculated from the single crystal X-ray structure (100 K) in black (bottom trace). The slight differences in peak position are attributable to lattice variations with temperature and preferred orientation.

In embodiments, the disclosure provides a composition comprising Form D, or a mixture of Forms D and A.

In embodiments, the disclosure provides Compound I as Form E, a dehydrated Form D. Form E can be produced by heating Form D of Compound I to approximately 60° C., with the conversion starting at approximately 40° C. As heating continues above approximately 70-75° C., Form E converts to Form A, the anhydrous form. Thus, Form E can be considered a meta-stable form. If Form E is cooled after its formation to approximately 35° C. or cooler, it converts to Form D. In embodiments, the disclosure provides a composition comprising Form E, or a mixture of Forms E and A, or a mixture of Forms E and D.

Form F is generally the most stable form at lower temperatures (e.g. between approximately 50 and 20° C.) and very high water activities. But the composition of the starting mixture also has an effect. While Form F is the stable form in pure water at 5° C. whether it is present in the starting mixture or not, at 20° C. in water, Form F is the more stable form when a mixture of Forms D and F is used. However, Form D is the kinetically more stable form when a mixture of Forms A and D is used.

Thus, Form F can be produced by slurrying amorphous Compound I or Form A in water alone at 5° C., or by lyophilizing amorphous Compound I from a t-butanol/water (50/50, v/v) mixture. Form F can also be produced at 5° C.

in an ethanol/water mixture (50/50, v/v) if seeds of Form F are present in the starting mixture using either Form A or Form D, but Form D is the stable form at 5° C. when a mixture of Forms A and D is used.

At 20° C. in water, Form F is the more stable form when a mixture of Forms D and F is used as the starting material. At 20° C. in water, Form D is the stable form when a mixture of Forms A and D is used.

These results indicate that in pure water at 5° C. Form F is the most stable form, but at 20° C. seeds of Form F need to be present to make the conversion to a stable Form F. Similarly, at 5° C. in ethanol/water 50/50 v/v Form F is the stable form when seeds of Form F are present in the starting mixture, but Form D is kinetically stable at 5° C. when a mixture of Forms A and D is used. Based on the observed spontaneous crystallization of Form F at low temperatures and high water activities, Form F may be formed in a formulation of Compound I that is initially Form D or a mixture of Forms A and D. Accordingly, in embodiments the disclosure provides a composition comprising Form F, or a mixture of Forms D and F, or a mixture of forms A, D, and F.

Drying Form F in a vacuum oven at room temperature results in its conversion to amorphous Compound I. Form F converts to Form A (a) upon heating, (b) by exposure to 40° C./20% relative humidity, or (c) upon storage at very low humidity in a dessicator at room temperature. In addition, cycling humidity, such as in a gravimetric vapor sorption experiment, results in Form F converting to Form D.

In embodiments, the disclosure provides Compound I in the form of the dihydrate Form D produced by subjecting Form A of Compound I to a wet granulation process using purified water as the granulating medium. In embodiments, the wet granulation process comprises a high shear mixing step (for example, an apparatus such as a Diosna® P ⅙ equipped with 1 L and 4 L bowls) followed by gentle milling (for example, in an apparatus such as a Comil®, to delump the granules). In embodiments, the process further comprises a step of drying the granules (for example, using a Strea Pro® Fluid Bed Drier). In embodiments, the granules are dried to a water content of not more than 4% w/w (as measured, e.g., by a moisture balance).

In embodiments, one or more excipients are added during the granulation process, either before granulation or after the granules have dried, in accordance with the knowledge in the pharmaceutical arts. In embodiments, the one or more excipients is selected from one or more of a filler material (e.g., lactose, sucrose, glucose, mannitol, sorbitol, calcium phosphate, calcium carbonate, and cellulose, including microcrystalline cellulose), a solution binder (e.g., gelatin, polyvinyl pyrrolidone, cellulose derivatives, such as hydroxypropyl methyl cellulose, polyethylene glycol, sucrose, and starch), a dry binder (e.g., cellulose, methyl cellulose, polyvinyl pyrrolidone, and polyethylene glycol), a disintegrant (e.g., starch, cellulose, crosslinked polyvinyl pyrrolidone, sodium starch glycolate, and sodium carboxymethylcellulose, including a cross-linked sodium carboxymethylcellulose such as croscarmellose sodium), a wetting agent (e.g., sodium lauryl sulfate), and a lubricant (e.g., magnesium stearate, stearic acid, polyethylene glycol, and sodium lauryl sulfate).

Pharmaceutical Compositions

The present disclosure also provides pharmaceutical compositions comprising one or more of Forms D, E, or F of Compound I, either alone or in a mixture with Form A as described above, and a pharmaceutically acceptable carrier or excipient. The term "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients are provided infra.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In embodiments, the chemical components of the pharmaceutical composition are substantially free from chemical impurities. The term "chemical purity" refers to the amount, usually given as a weight percentage, of a particular compound in a sample of the compound. Unless stated otherwise, percentages stated throughout this specification are weight/weight (w/w) percentages. In embodiments, the pharmaceutical composition comprises a pseudo-polymorphic form of Compound I that has a chemical purity greater than 98.0% as determined by HPLC. In embodiments, the pseudo-polymorph has a chemical purity of 99.0%. In embodiments, the pseudo-polymorph has a chemical purity of 99.5%. In embodiments, the pseudo-polymorph has a chemical purity of 99.9%.

The term "suitable solvent" refers to any solvent, or mixture of solvents, inert to the ongoing reaction that sufficiently solubilizes the reactants to afford a medium within which to effect the desired reaction.

The term "suspension" refers to a two-phase system consisting of a finely divided solid in amorphous, crystalline form, or mixtures thereof, dispersed (suspended) in a liquid or dispersing medium, usually the solvent. The term "slurry" refers to a suspension formed when a quantity of powder is mixed into a liquid in which the solid is only slightly soluble (or not soluble). "Slurrying" refers to the making of a slurry.

The term "amorphous" as used herein, means essentially without a regularly repeating arrangement of molecules or external face planes.

It is meant to be understood that peak heights in a powder x-ray diffraction pattern may vary and will be dependent on variables such as the temperature, crystal size, crystal habit, sample preparation or sample height in the analysis well.

It is also meant to be understood that peak positions may vary when measured with different radiation sources.

The type of formulation used for the administration of the polymorph employed in the methods of the present invention may be dictated by the type of pharmacokinetic profile desired from the route of administration and the state of the patient.

Formulations amenable to oral, sublingual, nasal or injectable administration are prepared in a manner well known in the pharmaceutical art and comprise at least one active compound. See, e.g., REMINGTON'S PHARMACEUTICAL SCIENCES, (16$^{th}$ ed. 1980).

In general, the disclosure provides a formulation or pharmaceutical composition that includes at least one active ingredient that is a pseudo-polymorph of Compound I as described herein. The formulations and pharmaceutical compositions may further comprise an additional active pharmaceutical ingredient (API). The formulations or pharmaceutical compositions typically comprise an excipient, are diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, gels, suppositories, sterile injectable solutions, and sterile packaged powders.

In preparing a formulation, it may be necessary to mill the active ingredient to provide the appropriate particle size prior to combining with the other ingredients. If the active ingredient is substantially insoluble, it ordinarily is milled to a particle size of less than 200 mesh. If the active ingredient is substantially water soluble, the particle size is normally adjusted by milling to provide a substantially uniform distribution in the formulation, e.g., about 40 mesh. In one embodiment of the present invention, the particle size range is between about 0.1 μm to about 100 μm.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations may include a filler such as lactose, sucrose, glucose, mannitol, sorbitol, calcium phosphate, calcium carbonate, and cellulose (including microcrystalline cellulose); lubricating agents such as talc, magnesium stearate, and mineral oil; wetting agents; emulsifying and suspending agents; solution or dry binders such as gelatin, polyvinyl pyrrolidone, cellulose, methyl cellulose, cellulose derivatives (e.g., hydroxypropyl methyl cellulose), polyethylene glycol, sucrose, starch, and polyethylene glycol; disintegrants such as starch, cellulose, crosslinked polyvinyl pyrrolidone, sodium starch glycolate, and sodium carboxymethylcellulose (including a cross-linked sodium carboxymethylcellulose such as croscarmellose sodium); preserving agents such as methyl- and propylhydroxybenzoates; sweetening agents; and flavoring agents.

The compounds of the invention can be formulated so as to provide quick, sustained or delayed release of the active ingredient after administration to the patient by employing procedures known in the art.

The following formulation examples are illustrative only and are not intended to limit the scope of the present invention. The term "active ingredient" refers to a pseudo-polymorph as described herein.

While it is possible to administer an active ingredient employed in the methods described here directly, without any formulation, the active ingredient is usually administered in the form of a pharmaceutical formulation comprising a pharmaceutically acceptable excipient and at least one active ingredient. Such formulations can be administered by a variety of routes including oral, buccal, rectal, intranasal, dermal, transdermal, subcutaneous, intravenous, intramuscular, and intranasal. The formulations employed in the methods described here are effective as both injectable and oral compositions.

In order to administer transdermally, a transdermal delivery device ("patch") is often needed. Such transdermal patches may be used to provide continuous or discontinuous infusion of a polymorph of the present invention in controlled amounts. The construction and use of transdermal patches for the delivery of pharmaceutical agents is well known in the art. See e.g., U.S. Pat. No. 5,023,252. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions which can transiently open the blood-brain barrier.

In embodiments, there is provided a pharmaceutical formulation comprising at least one active ingredient as described above in a formulation adapted for buccal and/or sublingual, or nasal administration. This embodiment provides administration of the active ingredient in a manner that avoids gastric complications, such as first pass metabolism by the gastric system and/or through the liver. This route of administration may also reduce adsorption times, providing more rapid onset of therapeutic benefit.

In embodiments, the disclosure provides a pharmaceutical composition comprising an amount of an active ingredient ranging up to 500 mg per dose administered once, twice, or three times daily, and a pharmaceutically acceptable diluent or carrier.

In embodiments, the disclosure provides a pharmaceutical composition for oral or rectal administration comprising an amount of an active ingredient as described herein ranging up to 500 mg per dose administered once, twice or three times daily, and a pharmaceutically acceptable diluent or carrier. In embodiments, the disclosure provides a pharmaceutical composition comprising an amount of an active ingredient as described herein wherein the amount is from 50 mg to 500 mg per dose. In embodiments, the disclosure provides a pharmaceutical composition comprising an amount of an active ingredient as described herein wherein the amount is from 50 mg to 400 mg per dose. In embodiments, the disclosure provides a pharmaceutical composition comprising an amount of an active ingredient as described herein wherein the amount is 50 mg per dose. In embodiments, the disclosure provides a pharmaceutical composition comprising an amount of an active ingredient as described herein wherein the amount is 100 mg per dose. In embodiments, the disclosure provides a pharmaceutical composition comprising an amount of an active ingredient as described herein wherein the amount is 200 mg per dose. In embodiments, the disclosure provides a pharmaceutical composition comprising an amount of an active ingredient as described herein wherein the amount is 400 mg per dose.

In embodiments, the disclosure provides a pharmaceutical composition comprising an active ingredient as described herein wherein the administration is oral. In embodiments, the disclosure provides a pharmaceutical composition comprising an amount of an active ingredient as described herein wherein the administration is rectal.

In embodiments, the disclosure provides a pharmaceutical composition for buccal, sublingual, nasal/intranasal, transdermal, subcutaneous, injectable, intravenous, or intramuscular administration comprising an amount of an active ingredient as described herein ranging up to 200 mg per dose administered once, two or three times daily and a pharmaceutically acceptable diluent or carrier.

In embodiments, the disclosure provides a pharmaceutical composition comprising an active ingredient as described herein wherein the amount is from 2 to 100 mg per dose. In embodiments, the invention relates to a pharmaceutical composition comprising an amount of an active ingredient as described herein wherein the amount is about 10, 15, 25, 30, 45 50, 60, 75, 90 or 100 mg per dose.

In embodiments, the disclosure provides a pharmaceutical composition, wherein the administration is buccal. In embodiments, the disclosure provides a pharmaceutical composition, wherein the administration is sublingual. In embodiments, the disclosure provides a pharmaceutical composition, wherein the administration is nasal or intranasal. In embodiments, the disclosure provides a pharmaceutical composition, wherein the administration is transdermal. In embodiments, the disclosure provides a pharmaceutical composition, wherein the administration is subcutaneous. In embodiments, the disclosure provides a pharmaceutical composition, wherein the administration is injectable. In embodiments, the disclosure provides a pharmaceutical composition, wherein the administration is intravenous. In embodiments, the disclosure provides a pharmaceutical composition, wherein the administration is intramuscular.

In embodiments, the disclosure provides a pharmaceutical composition, wherein the dose of an active ingredient as described herein is administered one time daily. In embodiments, the disclosure provides a pharmaceutical composition, wherein the dose of an active ingredient as described herein is administered two times daily. In embodiments, the disclosure provides a pharmaceutical composition, wherein the dose of an active ingredient as described herein is administered three times daily.

Methods of Use

The present disclosure also provides methods of treating migraine in a mammal comprising administering to a mammal in need of such treatment an effective amount of a pseudo-polymorph of Compound I, and mixtures thereof, as described herein. In embodiments, the pseudo-polymorph of Compound I is selected from Form D, Form E, and Form F of Compound I, and mixtures thereof, either alone or in combination with Form A, as described herein. In embodiments of any of the methods described here, the pseudo-polymorph of Compound I is selected from Form D, Form E, and Form F of Compound I, and mixtures thereof, including mixtures of one or more of Forms D, E, and F with Form A, as described herein. In embodiments, the mammal is a human.

In embodiments, the disclosure also provides methods for increasing activation of 5-$HT_{1F}$ receptors by administering an effective amount of a pseudo-polymorph of Compound I, and mixtures thereof, including mixtures with Form A, as described herein, while avoiding vasoconstrictive activity, for treating a variety of disorders that have been linked to decreased neurotransmission of serotonin in mammals. Included among these disorders are migraine, general pain, trigeminal neuralgia, dental pain or temporomandibular joint dysfunction pain, anxiety, general anxiety disorder, panic disorder, depression, disorders of sleep, chronic fatigue syndrome, premenstrual syndrome or late luteal phase syndrome, post-traumatic syndrome, memory loss, dementia including dementia of aging, social phobia, autism, attention deficit hyperactivity disorder, disruptive behavior disorders, impulse control disorders, borderline personality disorder, obsessive compulsive disorder, premature ejaculation, erectile dysfunction, bulimia, anorexia nervosa, alcoholism, tobacco abuse, mutism, and trichotillomania. The pseudo-polymorphs described here are also useful as a prophylactic treatment for migraine.

In those instances where the disorders which can be treated by serotonin agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The use of a pseudo-polymorph of Compound I selected from Forms D, E, and Form F of Compound I, and mixtures thereof, including mixtures with Form A, as described herein, for the activation of the 5-$HT_{1F}$ receptor, for the inhibition of neuronal peptide extravasation, in general or due to stimulation of the trigeminal ganglia specifically, and/or for the treatment of any of the disorders described above, are all embodiments of the present invention.

The term "effective amount" means an amount of a pseudo-polymorph described here which is capable of activating 5-$HT_{1F}$ receptors and/or inhibiting neuronal protein extravasation.

As used herein, "treating" or "treatment" includes any effect e.g., lessening, reducing, modulating, or eliminating, that results in the improvement of the condition, disease, disorder, etc. "Treating" or "treatment" of a disease state means the treatment of a disease-state in a mammal, particularly in a human, and include: (a) inhibiting an existing disease-state, i.e., arresting its development or its clinical symptoms; and/or (c) relieving the disease-state, i.e., causing regression of the disease state.

As used herein, "preventing" means causing the clinical symptoms of the disease state not to develop i.e., inhibiting the onset of disease, in a subject that may be exposed to or predisposed to the disease state, but does not yet experience or display symptoms of the disease state.

EXAMPLES

The following Examples are illustrative and should not be interpreted in any way so as to limit the scope of the invention.

Example 1: Preparation of Form D (Hydrate 1)

Form D can be prepared, for example, by any one of the following methods comprising (1) a wet granulation process starting with Form A, (2) storage of Form A at 25° C. and 96% relative humidity (RH), (3) recrystallization from solvent/water mixtures with high water activity, (4) storage of amorphous Compound I at 40° C. and 75% RH, (5) slurry of amorphous Compound I in solvent/water mixtures with high water activity, (6) forming a slurry of amorphous Compound I in water at room temperature or above, (7) forming a slurry of Form F in water at 37° C., (8) forming a competitive slurry of Form F, e.g. ethanol-water (50/50 v/v) at 20° C.

In a specific example, Hydrate 1 (Form D) was produced through a wet-granulation process using a Diosna P ⅙ high-shear granulator. 200 g of Form A of Compound I was mixed with water, in an amount from about 40 to 90% (w/v) in a 4 L bowl. Initial dry mixing of blend before fluid addition was kept as a constant factor (2 minutes, impeller speed as per related run, chopper off). A spray rate (g*kg/min) between 20 and 60 was used, with an impeller speed of 400-900 rpm which corresponds to 4.6-10.3 m/s tip speed. In clinical manufacturing on the Roto P10, the center point of this tip speed range corresponds to the tip speed on the Roto P10 (7.3 m/s). When manufacturing on the PMA65, the corresponding tip speed is 9.8 m/s. The massing time is between 0 and 2 minutes. The results of an experiment varying these parameters is shown below; all of these runs produced Hydrate 1 (Form D) as analyzed at the pre-drying stage. Only run 9 produced the dehydrated hydrate (Form E) upon drying; crystals produced by all other runs remained as Hydrate 1 upon drying.

| Run | Spray Rate (g * kg/min) | Impeller Speed (rpm) | Water amount (%) | Massing time (minutes) |
| --- | --- | --- | --- | --- |
| 1 | 20 | 400 | 87 | 2 |
| 2 | 60 | 400 | 87 | 0 |
| 3 | 40 | 650 | 66 | 1 |
| 4 | 40 | 650 | 66 | 1 |
| 5 | 60 | 900 | 45 | 0 |
| 6 | 40 | 650 | 66 | 1 |
| 7 | 20 | 400 | 45 | 0 |
| 8 | 60 | 400 | 45 | 2 |
| 9 | 20 | 900 | 45 | 2 |
| 10 | 20 | 900 | 87 | 0 |
| 11 | 60 | 900 | 87 | 2 |

The granule was dried into a fluid bed system with the following settings:
  inlet air volume: 60 m³/h
  inlet air temperature: 70° C.
  outlet product temperature: 22→34° C.
  product temperature: 23→50° C.
  drying time and loss on drying (LOD):
  70 min; LOD=13.2%
  160 min; LOD=5.1%
  235 min; LOD=4.9%
  290 min; LOD=4.3%
LOD was measured in a thermobalance by measuring weight loss after 15 minutes at 70° C.

Granule samples were taken after massing time (wet granule) and during the drying step (at 160 and 235 min). The samples were tested by XRPD and TGA. All the samples showed an XRPD pattern concordant with that of Hydrate 1 (Form D) obtained by water slurry. TGA data show similar weight loss for samples after 160 min and 235 min while a higher weight loss for the wet granule taken at the end of massing time.

In another specific example, Form D is made by slurrying Form A as follows: A saturated solution of Compound I Form A (50 mg/ml) was prepared with sufficient solid residual for XRPD, DSC, TGA and optical microscopy testing. The slurry was stirred for 4 hours and then the solid isolated and analyzed. The solid was tested "wet" and after drying with the XRPD, and only after drying with the other techniques. A new form called "Hydrate 1" (Form D) was found after slurry. The form remained the same after the drying of the material.

In another specific example, Form D is made from a scale-up production by slurrying amorphous material in MEK (methyl ethyl ketone)/water 95/5 v/v at 5° C. Slurrying Form A in water also produces Form D material, but during the re-crystallization, the sample became sticky, which could cause problems with stirring on a larger scale. In addition, a long period of stirring was required to fully crystallize the Form D material. Using amorphous material as the input material, with a high water activity solvent/water mixture, gave highly crystalline Form D material after stirring overnight at 5° C. MEK/water was chosen as the best solvent for crystallinity and yield.

Amorphous material was transferred to a glass reaction tube and weighed, giving a starting mass of amorphous material of 882 mg. The solid was cooled to 5° C. and 7.5 ml pre-cooled MEK/water 95/5 v/v was added, forming a suspension. After approximately 10 minutes stirring the sample was seeded with previously prepared Form D material. The sample was stirred at 5° C. (300 rpm) for 2½ days. A small amount of the suspension was filtered and air dried for 10 minutes prior to analysis by XRPD. The bulk sample was filtered through a 0.22 μm nylon filter and dried on the filter under suction for ~1 hour. The cake was broken up with a spatula and the powder was left to dry overnight at ambient conditions. The dried solid was weighed, giving a yield of 843.3 mg.

Characterization.

The Form D scale-up produced a crystalline, coarse white powder, which was consistent with the Form D reference diffractogram. ¹H NMR and KF analysis confirmed that this form is a dihydrate of the hemi succinate salt of Compound I. The sample was chemically pure—by HPLC, the purity was 99.9%. Microscopy revealed that the sample was composed of very small particles, arranged in agglomerates, which were porous due to the gaps between the tiny primary particles. The individual particles were an irregular shape with smooth surfaces Example 2: Preparation of Form F Form F can be prepared, for example, by starting with amorphous Compound I and forming a slurry in water at 5° C.; or one can form a competitive slurry starting with Form A seeded with Form F in water at 20° C., or in ethanol/water (50:50) at 5° C.

A. Scale-up. Amorphous samples of Compound I were transferred to a glass reaction tube and weighed, giving a starting mass of amorphous material of 913 mg. The solid was cooled to 5° C. and 12.5 ml pre-cooled water was added, forming a thick suspension. After approximately 10 minutes stirring the sample was seeded with ~10 mg previously prepared Form F material. The sample was stirred at 5° C. (300 rpm) for 2½ days. A small amount of the suspension was filtered and air dried for 10 minutes prior to analysis by XRPD. The bulk sample was filtered through a 0.22 μm nylon filter and dried on the filter under suction for ~1 hour. The cake was broken up with a spatula and the powder was left to dry overnight at ambient conditions. The dried solid was weighed, giving a yield of 874.5 mg.

B. Characterization. The Form F scale-up produced a crystalline, fine white powder, which was consistent with the Form F reference diffractogram. ¹H NMR and KF analysis confirmed that this form is a non-solvated trihydrate of the hemi succinate salt of Compound I. The sample was chemically pure, by HPLC it was 100% pure. The sample was composed of very small particles, arranged in loosely bound agglomerates. The individual particles were an irregular shape with smooth surfaces and there were some drusy particles.

Example 3: X-Ray Powder Diffraction Analysis of Forms D and F

A. Bruker AXS C2 GADDS

X-Ray Powder Diffraction (XRPD) patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analyzed and presented using Diffrac Plus EVA v15.0.0.0.

For studies done under ambient conditions, samples were prepared as flat plate specimens using powder of the indicated Form. Approximately 1-2 mg of the sample was lightly pressed on a glass slide to obtain a flat surface. For studies done under non-ambient conditions, samples run under non-ambient conditions were mounted on a silicon wafer with heat-conducting compound. The sample was then heated to the appropriate temperature at 10° C./min and subsequently held isothermally for 1 minute before data collection was initiated.

B. Bruker AXS D8 Advance

XRPD patterns were collected on a Bruker D8 diffractometer using Cu Kα radiation (40 kV, 40 mA), θ-2θ goniometer, and divergence of V4 and receiving slits, a Ge monochromator and a Lynxeye detector. The software used for data collection was Diffrac Plus XRD Commander v2.6.1 and the data were analyzed and presented using Diffrac Plus EVA v15.0.0.0.

Samples were run under ambient conditions as flat plate specimens using powder of the indicated Form. The sample was gently packed into a cavity cut into polished, zero-background (510) silicon wafer. The sample was rotated in its own plane during analysis. The details of the data collection are:
angular range: 2 to 42° 2θ; step size: 0.05° 2θ; Collection time: 0.5 s/step.

C. PANalytical Empyrean

XRPD patterns were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel3D detector, placed on the diffracted beam, was fitted with a receiving slit and 0.04 rad Soller slits. The software used for data collection was X'Pert Data Collector v. 5.3 and the data were analyzed and presented using Diffrac Plus EVA v. 15.0.0.0 or Highscore Plus v. 4.5.

Samples were prepared and analyzed in either a metal or Millipore 96 well-plate in transmission mode. The metal well-plate is made up of an X-ray transparent film sandwiched between two metal sheets. Dry powders (approximately 5 mg) were lightly pressed into the wells for analysis. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate.

The details of the data collection are: angular range: 2.5 to 32.0° 2θ; step size: 0.0130° 2θ; collection time: total collection time of 2.07 min. A longer method was also used: Angular range: 2.5 to 42.0° 2θ; step size: 0.0130° 2θ; collection time: total collection time of 8.0 min.

Variable temperature XRPD (VT-XRPD) experiments were carried out with the samples mounted on a metal sample holder (with silicon insert) with heat-conducting compound. The sample was then heated in air to the appropriate temperature at 5° C./min. The sample was analyzed at the selected temperatures using the 8 minute method (as above).

D. Results for Form D and Form F. The XRPD for Form D is shown in FIG. 1A; for Form F in FIG. 1B. For Form D, VT-XRPD showed a gradual conversion (40-60 C) to Form E on heating, which was reversible, as Form E converted back to Form D upon cooling to 35 C. Additional heating (80-95 C) caused Form E to convert to Form A. For Form F, VT-XRPD showed a loss of crystallinity at 70 C, conversion to partially crystalline Form A by 75 C, but required further heating (to 100 C) to fully crystallize to Form A.

Example 4: Single Crystal X-Ray Diffraction (SCXRD)

Data were collected on a Rigaku Oxford Diffraction Supernova Dual Source, Cu at Zero, Atlas CCD diffractometer equipped with an Oxford Cryosystems Cobra cooling device. The data was collected using CuKα radiation. Structures were solved using the SHELXTL (Sheldrick, 2013) programs and refined with the SHELXTL program as part of the Bruker AXS SHELXTL suite (V6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter. SCXRD for Form D is shown in FIG. 1D.

TABLE 1

Single crystal data for Compound I Form D.

| | |
|---|---|
| Crystallization Solvent | Water |
| Crystallization Method | Evaporation |
| Empirical formula | $C_{21}H_{25}F_3N_3O_6$ |
| Formula weight | 472.44 |
| Temperature | 100(2) K |
| Wavelength | 1.54178 Å |
| Crystal size | 0.200 × 0.150 × 0.100 mm |
| Crystal habit | colorless block |
| Crystal system | monoclinic |
| Space group | C2/c |
| Unit cell dimensions | a = 25.0800(7) Å   α = 90° |
| | b = 10.08215(13) Å   β = 123.714(4)° |
| | c = 20.8357(9) Å   γ = 90° |
| Volume | 4382.4(3) Å$^3$ |
| Z | 8 |
| Density (calculated) | 1.432 Mg/m$^3$ |
| Absorption coefficient | 1.048 mm$^{-1}$ |
| F(000) | 1976 |

TABLE 2

Compound I Form D XRPD Peak Listing
Compound I Form D

| 2θ° | Intensity (%) |
|---|---|
| 8.5 | 38.7 |
| 9.7 | 31.4 |
| 11.9 | 14.2 |
| 13.8 | 76.8 |
| 14.0 | 67.4 |
| 15.4 | 12.5 |
| 15.5 | 10.4 |
| 15.8 | 44.5 |
| 17.0 | 45.5 |
| 17.3 | 4.2 |
| 17.7 | 6.8 |
| 18.0 | 58.7 |
| 18.7 | 9.0 |
| 18.9 | 13.4 |
| 19.3 | 27.1 |
| 19.8 | 4.7 |
| 20.0 | 27.8 |
| 20.8 | 4.3 |
| 21.4 | 25.1 |
| 21.6 | 10.6 |
| 21.9 | 10.0 |
| 22.4 | 25.5 |
| 22.7 | 10.6 |
| 23.0 | 7.5 |
| 24.1 | 100.0 |
| 24.3 | 11.8 |
| 24.7 | 17.5 |
| 25.6 | 10.4 |
| 25.9 | 39.4 |
| 26.1 | 17.1 |
| 26.4 | 69.6 |
| 27.0 | 20.9 |
| 27.5 | 13.1 |
| 27.8 | 17.8 |
| 28.4 | 14.6 |
| 29.1 | 14.6 |
| 29.6 | 11.2 |
| 29.8 | 8.2 |
| 31.9 | 12.4 |

Representative peaks of the X-ray diffraction pattern for Form D include peaks at about 18.7, 26.5, 27.0, 27.5 and 27.8 degrees 2θ using Cu-K$_\alpha$ radiation.

TABLE 3

Compound I Form E XRPD Peak Listing
Compound I Form E

| 2θ° | Intensity (%) |
|---|---|
| 8.4 | 100.0 |
| 9.2 | 9.5 |
| 9.7 | 28.4 |
| 9.8 | 69.1 |
| 10.5 | 15.5 |
| 11.9 | 12.0 |
| 12.1 | 37.5 |
| 12.5 | 8.4 |
| 13.9 | 48.6 |
| 14.2 | 89.3 |
| 15.4 | 17.5 |
| 15.6 | 8.4 |
| 15.9 | 33.4 |
| 16.3 | 26.2 |
| 16.4 | 23.9 |
| 16.8 | 19.5 |
| 16.9 | 20.3 |
| 17.0 | 19.8 |
| 17.5 | 6.4 |
| 17.8 | 7.2 |
| 18.1 | 33.5 |
| 18.3 | 57.6 |
| 18.8 | 6.7 |
| 19.0 | 10.1 |
| 19.4 | 15.7 |
| 19.7 | 14.8 |
| 20.2 | 19.5 |
| 20.5 | 27.7 |
| 20.7 | 8.1 |
| 21.1 | 15.2 |
| 21.5 | 20.6 |
| 22.0 | 13.9 |
| 22.3 | 11.0 |
| 22.6 | 25.0 |
| 22.9 | 8.1 |
| 23.5 | 11.4 |
| 24.3 | 43.3 |
| 24.5 | 52.0 |
| 24.8 | 11.7 |
| 25.5 | 13.1 |
| 26.0 | 23.0 |
| 26.7 | 64.3 |
| 27.1 | 14.2 |
| 27.7 | 11.3 |
| 28.0 | 11.9 |
| 28.5 | 23.6 |
| 29.3 | 10.8 |
| 29.9 | 16.9 |
| 30.5 | 8.7 |
| 32.2 | 12.3 |

Representative peaks of the X-ray diffraction pattern for Form E include peaks at about 9.2 and 10.5 degrees 2θ using Cu-K$_\alpha$ radiation.

TABLE 4

Compound I Form F XRPD Peak Listing
Compound I Form F

| 2θ° | Intensity (%) |
|---|---|
| 8.6 | 25.4 |
| 10.3 | 12.9 |
| 12.3 | 100.0 |
| 12.7 | 6.3 |
| 14.2 | 6.5 |
| 14.3 | 4.9 |
| 15.2 | 2.5 |
| 16.0 | 4.2 |
| 17.1 | 42.6 |
| 19.2 | 15.1 |
| 19.5 | 4.3 |
| 20.0 | 15.0 |
| 20.3 | 5.1 |
| 20.6 | 34.2 |
| 21.4 | 6.3 |
| 21.5 | 10.0 |
| 22.1 | 23.6 |
| 23.3 | 10.5 |
| 23.5 | 5.4 |
| 24.2 | 29.9 |
| 25.1 | 9.7 |
| 25.5 | 9.7 |
| 25.6 | 10.2 |
| 26.3 | 6.0 |
| 26.9 | 26.2 |
| 27.5 | 7.2 |
| 28.5 | 5.6 |
| 29.3 | 8.2 |
| 30.1 | 17.0 |
| 31.7 | 7.7 |
| 32.1 | 7.4 |

The data for the observed and representative peaks of Compound I Form A as reported in Carniaux U.S. Pat. No. 8,697,876 are presented in Tables 5 and 6, respectively, for reference.

TABLE 5

Compound I Form A XRPD Peak Listing

| 2θ | Intensity (%) |
|---|---|
| 7.67 ± 0.10 | 27 |
| 9.61 ± 0.10 | 33 |
| 11.06 ± 0.10 | 21 |
| 13.38 ± 0.10 | 23 |
| 14.07 ± 0.10 | 41 |
| 15.11 ± 0.10 | 51 |
| 15.32 ± 0.10 | 62 |
| 16.15 ± 0.10 | 44 |
| 16.39 ± 0.10 | 100 |
| 16.81 ± 0.10 | 47 |
| 18.47 ± 0.10 | 43 |
| 19.33 ± 0.10 | 61 |
| 21.51 ± 0.10 | 28 |
| 22.14 ± 0.10 | 53 |
| 23.18 ± 0.10 | 46 |
| 23.39 ± 0.10 | 46 |
| 23.56 ± 0.10 | 59 |
| 23.84 ± 0.10 | 33 |
| 24.77 ± 0.10 | 36 |
| 25.01 ± 0.10 | 24 |
| 25.91 ± 0.10 | 52 |
| 26.68 ± 0.10 | 20 |
| 28.65 ± 0.10 | 19 |
| 29.31 ± 0.10 | 12 |

TABLE 6

Compound I Form A Representative XRPD Peak Listing

| 2θ | Intensity (%) |
|---|---|
| 15.32 ± 0.10 | 62 |
| 16.39 ± 0.10 | 100 |
| 19.33 ± 0.10 | 61 |
| 22.14 ± 0.10 | 53 |
| 23.56 ± 0.10 | 59 |
| 25.91 ± 0.10 | 52 |

Example 5: Comparative Analysis of Selected XRPD Peaks for Form a, D and E

For comparison, FIG. 1E-G shows partial XRPD patterns of Form D (blue line); Form A (green); Form E (red). For Form A, a distinctive peak is noted at approximately (+0.2° 2θ) 7.7° 2θ. For Form D, peaks at approximately (±0.2° 2θ) 18.7° 2θ, 26.5° 2θ, 27.0° 2θ, 27.5° 2θ and 27.8° 2θ are distinctive. For Form E, distinctive peaks are noted at approximately (±0.2° 2θ) 9.2° 2θ and 10.5° 2θ.

As evidenced by the data presented above, Forms D, E, and F of Compound I each have a unique XRPD pattern which can be used to differentiate each of these forms from Form A of Compound I.

Example 6: Nuclear Magnetic Resonance (NMR)

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-d6, unless otherwise stated. Off-line analysis was carried out using ACD Spectrus Processor 2014.

As shown in FIG. 5, the solution state $^1$H-NMR spectrum of dissolved forms D or F is consistent with the hemisuccinate of Compound I crystallized from methyl ethyl ketone (present at 0.03 mole eq., 0.4 wt %), showing 0.5 mole equivalent of succinic acid.

Example 7: Thermal Analyses (A) Differential Scanning Calorimetry (DSC)
DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminum pan, was heated at 10° C./min from 25° C. to 250° C. A purge of dry nitrogen at 50 ml/min was maintained over the sample.

Modulated temperature DSC was carried out using an underlying heating rate of 2° C./min and temperature modulation parameters of +0.64° C. (amplitude) every 60 seconds (period).

The instrument control software was Advantage for Q Series v2.8.0.394 and Thermal Advantage v5.5.3 and the data were analyzed using Universal Analysis v4.5A.

(B) Thermo-Gravimetric Analysis (TGA)
TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminum DSC pan and heated at 10° C./min from ambient temperature to 350° C. A nitrogen purge at 60 ml/min was maintained over the sample. The instrument control software was Advantage for Q Series v2.5.0.256 and Thermal Advantage v5.5.3 and the data were analyzed using Universal Analysis v4.5A.

(C) Results of DSC and TGA for Form D and Form F.
Overlays of DSC and TGA results for Form D are shown in FIG. 2 and for Form F in FIG. 3.

For Form D, the TGA showed a 7.5 wt. % loss from 25-110 C, corresponding to 2.0 mole equivalents water, with degradation around 200 C. The DSC analysis showed a broad endotherm onset at 53.1 C (−158.2 J/g), reflecting the loss of water, a broad exotherm onset at 92.1 C (−24.9 J/g) upon re-crystallization, and a sharp endotherm onset, reflecting melting, at 197.9 C (−119.0 J/g).

For Form F, the TGA showed an 11.4 wt. % loss from 25-150 C, corresponding to 3.1 mole equivalents water, with degradation around 200 C. The DSC analysis showed a broad endotherm onset at 71.2 C (−198.4 J/g), a shallow endotherm (2 peaks) onset at 95.7 C (−6.4 J/g), a shallow exotherm (2 peaks) onset at 103.4 C (26.9 J/g) and a sharp endotherm onset at 197.8 C (−114.4 J/g), reflecting melting.

Example 8: Microscopy

A. Polarized Light Microscopy (PLM)
A. 1. Leica LM/DM Polarized Light Microscope
Samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarized light, coupled to a λ false-color filter.

A.2. Nikon LM/DM Polarized Light Microscope

Samples were studied on a Nikon SMZ 1500 polarized light microscope with a digital video camera connected to a DS Camera control unit DS-L2 for image capture. A small amount of each sample was placed on a glass slide, mounted in immersion oil, the individual particles being separated as well as possible. The sample was viewed with appropriate magnification and partially polarized light, coupled to a λ false-color filter.

B. Scanning Electron Microscopy (SEM)

Data were collected on a Phenom Pro Scanning Electron Microscope. A small quantity of sample was mounted onto an aluminum stub using conducting double-sided adhesive tape. A thin layer of gold was applied using a sputter coater (20 mA, 120 s).

Example 9: Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. Data collection and analysis using Tiamo v2.2.

For Form D, a 7.6 wt. % loss was detected, corresponding to 2.0 mole equivalent water thus confirming the dihydrate form. For Form F, an 11.6 wt. % loss was detected, corresponding to 3.2 mole equivalents water, thus confirming the trihydrate form.

Example 10: Chemical Purity Determination by HPLC

As shown in FIG. 4A, the HPLC trace of Form D showed a chemical purity of 99.93%; and in FIG. 4B, the HPLC trace of Form F showed a chemical purity of 99.95%.

Purity analysis was performed on an Agilent HP1100 series system equipped with a diode array detector and using ChemStation software vB.04.03 using the method detailed below:

| Parameter | Value |
| --- | --- |
| Type of method | Reverse phase with gradient elution |
| Sample Preparation | 0.4 mg/ml in acetonitrile:water 1:1 |
| Column | Supelco Ascentis Express C18, 100 × 4.6 mm, 2.7 μm |
| Column Temperature (° C.) | 25 |
| Injection (μl) | 5 |
| Wavelength, Bandwidth (nm) | 255, 90 |
| Flow Rate (ml/min) | 2 |
| Phase A | 0.1% TFA in water |
| Phase B | 0.085% TFA in acetonitrile |

| Timetable | Time (min) | % Phase A | % Phase B |
| --- | --- | --- | --- |
| | 0 | 95 | 5 |
| | 6 | 5 | 95 |
| | 6.2 | 95 | 5 |
| | 8 | 95 | 5 |

Example 11: Dynamic Vapor Sorption (DVS)

Sorption isotherms were obtained using a SMS DVS Intrinsic moisture sorption analyser, controlled by DVS Intrinsic Control software v1.0.1.2 (or v1.0.1.3). The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was carried out using Microsoft Excel using DVS Analysis Suite v6.3.

| Parameter | Value |
| --- | --- |
| Adsorption-Scan 1 | 40-90 |
| Desorption/Adsorption-Scan 2 | 90-0, 0-40 |
| Intervals (% RH) | 10 |
| Number of Scans | 2 |
| Flow rate (ml/min) | 200 |
| Temperature (° C.) | 25 |
| Stability (° C./min) | 0.2 |
| Sorption Time (hours) | 6 hour time out |

Results.

Form D showed a large weight loss during the 10% RH step but the weight was gained as soon as the humidity was increased to 20% RH. The residue from the DVS experiment was mainly Form D but some peaks consistent with Form F were seen, showing that Form D is not completely stable at low relative humidities.

Form F showed little change in mass until the first 0% RH step, when a 9.6 wt % loss (2.6 mole equivalents of water) was observed before the experiment timed out (FIG. 7). It is likely that the full three moles of water would be lost, if the sample was held at 0% RH for longer than the maximum step time of 6 hours. When the humidity was increased, the sample gained weight steadily until 70% RH, when a weight gain was followed by a weight loss (typical of a crystallization event). It then crystallized at the 70% RH step, once it had gained enough water. The behavior in the second cycle was similar but with an overall weight loss, consistent with the crystallized material being the dihydrate and not the trihydrate starting material. This was confirmed by analyzing the residue from the DVS experiment (which was a crunchy solid) and was mainly Form D but with some Form F. These results show that Form F is not stable at low relative humidities.

Example 12: Thermodynamic Aqueous Solubility

Method.

Aqueous solubility was determined by suspending sufficient compound in water to give a maximum final concentration of ≥23 mg/ml of the parent free-form of the compound. The suspension was equilibrated at 37° C. for 24 hours then the pH was measured. The suspension was then filtered through a glass fiber C filter. The filtrate was then diluted by an appropriate factor. Quantitation was by HPLC with reference to a standard solution of approximately 0.2 mg/ml in DMSO. Different volumes of the standard, diluted and undiluted sample solutions were injected. The solubility was calculated using the peak areas determined by integration of the peak found at the same retention time as the principal peak in the standard injection. The solubility quoted is for the parent 'free form' of Compound I.

| Parameter | Value |
|---|---|
| Type of method | Reverse phase with gradient elution |
| Column | Phenomenex Luna, C18 (2) 5 μm 50 × 4.6 mm |
| Column Temperature (° C.) | 25 |
| Standard Injections (μl) | 1, 2, 3, 4, 5, 7 |
| Test Injections (μl) | 1, 2, 3, 10, 15, 20 |
| Detection: Wavelength, Bandwidth (nm) | 260, 90 |
| Flow Rate (ml/min) | 2 |
| Phase A | 0.1% TFA in water |
| Phase B | 0.085% TFA in acetonitrile |

| Timetable | Time (min) | % Phase A | % Phase B |
|---|---|---|---|
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Results

Slurrying Form D in water at 37° C. did not cause a change in form and the thermodynamic solubility was measured at 6.2-6.4 mg/ml (free form, corrected for the water and counter-ion content of the hemi-succinate dihydrate). Conversion to the trihydrate Form F did not occur at this temperature. The pH of the unfiltered saturated solution was 7.0.

Slurrying Form F in water at 37° C. caused a conversion to Form D. Initially the sample was highly soluble (kinetic solubility of Form F~32 mg/ml) but over the time, solid consistent with Form D began to precipitate out slowly. The thermodynamic aqueous solubility of this sample (Form D) was measured after 24 hours at 8.6 mg/ml (free form, corrected for the water and counter-ion content of the hemi succinate dihydrate). It is not possible to measure a thermodynamic aqueous solubility value for Form F at 37° C., as Form F is not stable at these conditions, as it converts to Form D. The pH of the unfiltered saturated solution was 7.2.

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

We claim:

1. A crystalline Form D di-hydrate of the hemisuccinate salt of 2,4,6-trifluoro-N-[6-(1-methyl-piperidine-4-carbonyl)-pyridin-2-yl]-benzamide characterized by an X-ray diffraction pattern when measured using Cu-K$_\alpha$ radiation having at least peaks at about 18.7+/−0.2 degrees 2θ, 26.5+/−0.2 degrees 2θ, 27.0+/−0.2 degrees 2θ, 27.5+/−0.2 degrees 2θ and 27.8+/−0.2 degrees 2θ.

2. The crystalline di-hydrate of claim 1, wherein the X-ray diffraction pattern includes at least one or more additional peaks selected from the group consisting of the following peaks at about degrees 2θ, +/−0.2 degrees 2θ, using Cu-K$_\alpha$ radiation:

8.5
9.7
11.9
13.8
14.0
15.4

-continued 15.5
15.8
17.0
17.3
17.7
18.0
18.7
18.9
19.3
19.8
20.0
20.8
21.4
21.6
21.9
22.4
22.7
23.0
24.1
24.3
24.7
25.6
25.9
26.1
26.4
27.0
27.5
27.8
28.4
29.1
29.6
29.8, and
31.9.

3. The di-hydrate of claim 1, produced by a method comprising wet granulation of amorphous Compound I.

4. A pharmaceutical composition comprising the di-hydrate of claim 1 and a pharmaceutically acceptable carrier.

5. The pharmaceutical composition of claim 4, wherein said di-hydrate is substantially free from impurities.

6. The pharmaceutical composition of claim 5, wherein said di-hydrate has a chemical purity greater than 98.0% as determined by HPLC.

7. A method of treating migraine in a human in need thereof comprising administering to a mammal in need of such treatment an effective amount of the di-hydrate of claim 1.

* * * * *